United States Patent [19]

Della Valle et al.

[11] Patent Number: 5,484,775
[45] Date of Patent: Jan. 16, 1996

[54] SEMISYNTHETIC GANGLIOSIDE ANALOGUES

[75] Inventors: Francesco Della Valle, Padova; Aurelio Romeo, Rome, both of Italy

[73] Assignee: FIDIA S.p.A., Abano Terme, Italy

[21] Appl. No.: 96,853

[22] Filed: Jul. 26, 1993

Related U.S. Application Data

[63] Continuation of Ser. No. 558,012, Jul. 26, 1990, abandoned.

[30] Foreign Application Priority Data

Jul. 27, 1989 [IT] Italy .................................. 48246/89

[51] Int. Cl.$^6$ ........................... A61K 31/715; C07H 5/04
[52] U.S. Cl. ................. 514/54; 514/25; 514/53; 514/61; 536/4.1; 536/53; 536/55.1; 536/55.3; 536/123
[58] Field of Search ................... 536/4.1, 53, 55, 536/55.3, 126; 514/54, 25, 53, 61

[56] References Cited

U.S. PATENT DOCUMENTS

| | | | |
|---|---|---|---|
| 4,476,119 | 10/1984 | della Valle et al. | 514/54 |
| 4,593,091 | 6/1986 | della Valle et al. | 536/53 |
| 4,713,374 | 12/1987 | della Valle et al. | 514/54 |
| 4,716,223 | 12/1987 | della Valle et al. | 536/53 |
| 4,990,604 | 2/1991 | Ogawa et al. | 536/17.9 |
| 5,010,059 | 4/1991 | Schmidt et al. | 536/17.9 |
| 5,350,841 | 9/1994 | Romeo et al. | 536/53 |

FOREIGN PATENT DOCUMENTS

| | | |
|---|---|---|
| 0167449 | 1/1986 | European Pat. Off. . |
| 0315113 | 5/1989 | European Pat. Off. . |
| 0328420 | 8/1989 | European Pat. Off. . |
| 0373039 | 6/1990 | European Pat. Off. . |

OTHER PUBLICATIONS

J. of Pharm. & Exper. Ther; vol. 252 No., Manev et al.
G. A. Nores et al., Methods in Enzymology, vol. 179 (1989) pp. 242–253.
S. Sonnino et al., Journal of Lipid Research, vol. 26, No. 2 (1985) pp. 248–257.
Y. Hirabayashi et al., J. Bioche., vol. 103, No. 1 (1988) pp. 1–4.
Acta Psychiat. Scand. 55, 102, (1977).
Eur. Medicophys., 13, 1, (1977).
Adv. Exp. Med. Biol. 71, 275 (1976).
Electromyogr. Clin, Neurophysiol. 19, 353, (1979).
Minerva Medica, 69, 3277, (1978).
Minerva Stomat. 27, 177, (1978).
Med. del Lavoro, 68, 296 (1977).
Brain Res. 197, 236, (1980).
J. of Neurochem. 37, 350 (1981).
Glycolipid Methodology, Robert W. Ledeen and Robert K. Yu, pp. 186–215, Chapter IX and X (1976).
Song et al., Biochemistry 28:4194–4200 (1989).
Glycolipid Methodology, Eric G. Brunngraber; Gudio Tettamantio and Bruno Berra; pp. 158–187; Chapter III. (1976).
Neuenhofer et al., Biochemistry 24:525–532 (1985).

*Primary Examiner*—Douglas W. Robinson
*Assistant Examiner*—Anita Varma
*Attorney, Agent, or Firm*—Birch, Stewart, Kolasch & Birch

[57] ABSTRACT

N-acyl-N,N'-dilysogangliosides, wherein the acyl groups are derived from unsubstituted aliphatic acids having from 1 to 11 carbon atoms, and N'-acyl-N,N'-dilysogangliosides and N,N'-di-acyl-N,N'-dilysogangliosides, in which the acyl groups are derived from unsubstituted aliphatic acids having from 1 to 24 carbon atoms (with the exception of certain acetyl and diacetyl derivatives). The compounds of the invention exhibit an inhibiting action on protein kinase C activation and, thus, can be utilized in therapies for various pathologies of the nervous system. Pharmaceutical compositions and therapeutic utilities for the lysoganglioside derivatives are also disclosed.

6 Claims, 2 Drawing Sheets

SEMISYNTHETIC GANGLIOSIDE ANALOGUES

This application is a continuation of application Ser. No. 07/558,012 filed on Jul. 26, 1990, now abandoned.

The present invention concerns semisynthetic ganglioside analogues and more precisely N-acyl-N,N'-di-lysogangliosides, in which the acyl groups are derived from unsubstituted aliphatic acids having from 1 to 11 carbon atoms, N'-acyl-N,N'-di-lyso-gangliosides and N,N'-diacyl-N,N'-di-lyso-gangliosides, in which the acyl groups are derived from unsubstituted aliphatic acids having from 1 to 24 carbon atoms, but only from 1 to 11 carbon atoms on the sphingosine nitrogen in the case of diacyl derivatives in which the N'-acyl group is acetyl, and functional derivatives of these compounds and the salts of all these compounds.

Gangliosides are generally mixtures of various unitary chemical compounds, identifiable by an approximate formula of the following kind:

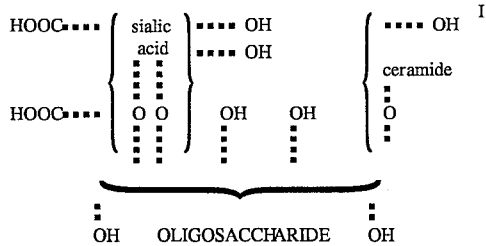

including an oligosaccharide part, generally well-defined chemically for each ganglioside, a sialic part (i.e. constituted by one or more sialic acids) and a ceramide part, the last three parts generally being constituted by a mixture of various sialic acids and various ceramide residues.

Sialic acids are acylated derivatives of neuraminic acid with the following formula:

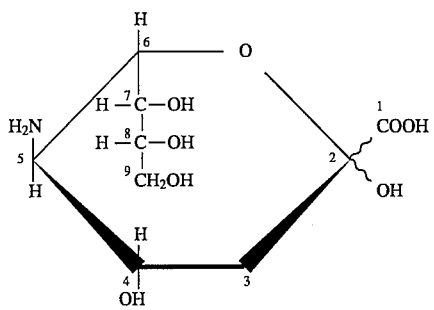

in which the amino group is acylated with acetic or glycolic acid and wherein the hydroxyl groups may also be esterified with these acids.

The ceramide group represents a N-acylsphingosine corresponding to one of the two formulae

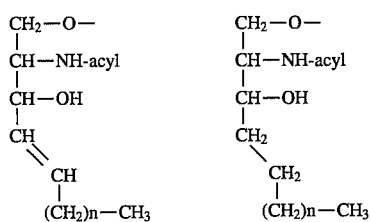

in which n=6–18 and the acyl group is derived from a saturated or unsaturated fatty acid having from 16 to 22 carbon atoms or from a corresponding hydroxyacid.

As already noted, the sialic and ceramide residues in gangliosides are mixtures of groups with the above formulae and this is also true of the purified gangliosides described in the literature.

The number of sialic acids present in gangliosides usually varies between 1 and 5. The sialic residues are bound to the oligosaccharide by a ketose bond formed by the hydroxyl in the 2-position with a hydroxyl of the oligosaccharide.

When several sialic acids are bound to each other, their molecules are united by ketose bonds formed between the hydroxyls of positions 2 and 8 of two sialic acid molecules. The sialic acids of gangliosides, including the aforesaid purified gangliosides, are mixtures of various chemically unitary acids, for example N-acetylneuraminic and N-glycolylneuraminic acids, in which the former is predominant, and optionally of one or more of their O-acyl derivatives, for example 8-O-acyl derivatives. Oligosaccharides are composed of a maximum of 5 monosaccharides or their derivatives with an acylamino group, especially hexoses and their derivatives of the aforesaid type. At least one glucose or galactose molecule is always present in the oligosaccharide; the most frequent residues as acylamino derivatives of the aforesaid sugars are N-acetylglucosamine and N-acetylgalactosamine.

The term "lysoganglioside" is used in the literature to describe compounds derived from natural gangliosides by the elimination of the acyl group present on the sphingosine nitrogen. This elimination can be effected enzymatically, for example by exposing the gangliosides to the action of glycosphingolipid-ceramide-deacylase enzyme. By using this type of hydrolysis it is possible to leave intact the acylamino and acylhydroxyl groups of neuraminic acid. To deacylate these groups also and thus obtain a ganglioside derivative containing two free amino groups, both on the sphingosine nitrogen and on the neuraminic nitrogen, chemical hydrolysis must be used, for example with dilute potassium hydroxide. The ganglioside derivatives obtained by deacylation on the neuraminic nitrogen as previously described are usually described in the literature as "de-N-acetylgangliosides", since the acyl group in this position is mainly the acetyl group. By naming the two nitrogen atoms in the sphingosine and neuraminic residues N and N' respectively, the nomenclature "N'-lysoganglioside" can be used for the aforesaid de-N-acetyl-gangliosides, in the same way as the term lysogangliosides is used for derivatives with a free amino group in the sphingosine residue, which should therefore be more precisely identified as "N-lysogangliosides". The term N,N'-di-lyso-gangliosides on the other hand, refers to the compound with both free amino groups. As already noted above, this nomenclature will be used in the present application.

The aforesaid definition of derivatives according to the invention encompasses the group of ganglioside derivatives presenting an acetyl group on the neuraminic nitrogen and a $C_{1-11}$ acyl on the sphingosine nitrogen.

The invention also encompasses N-acyl-lysogangliosides of this type derived from the aforesaid lysogangliosides obtained enzymatically and with, therefore, acyl groups in the sialic acids as present in natural gangliosides, and that is, mixtures of acylamino groups derived mostly from acetic acid and to a lesser degree from glycolic acid, and optionally with acyl groups esterifying the hydroxy groups. The term "N-lysogangliosides" or "N-acyl-lysogangliosides" will therefore be used in the following description of the invention both for these derivatives, which will be qualified as "natural" (for example, natural N-lyso $GM_1$), and for those with a unitary acetyl group on the neuraminic nitrogen, which will be named without this addition, or preferably as a derivative of N,N'-di-lysogangliosides, for example N,N'-di-acetyl-N,N'-di-lyso $GM_3$. The term "acyl-di-lysogangliosides" will however be used hereafter also to signify all the new compounds of the invention. As will be expounded hereafter, it is possible to selectively deacylate a ganglioside on the nitrogen and on the neuraminic hydroxy groups, for example with a dilute alkaline hydroxide. In these compounds, acylation of the amino group of the neuraminic residue with a different acyl from the acetyl (and glycolyl) produces N,N'-diacyl-N,N'-di-lysogangliosides which conserve a natural part of gangliosides, that is the mixed acyl group derived from higher aliphatic acids. These derivatives, which constitute a preferential group of the new compounds according to the present invention, will be named N'-acyl-N'-lysogangliosides, for example N'-propionyl-N'-lyso $GM_1$, N'-pivaloyl-N'-lyso $GM_3$, N'-stearoyl-N'-lyso $GM_1$, etc.

The new compounds of the present invention are semisynthetic ganglioside analogues differing from gangliosides on account of the presence of unitary and well-defined acyl groups on the sphingosine and/or neuraminic nitrogen (with the exception of natural N-acyl-N-lysogangliosides and N'-acyl-N'-lysogangliosides) and the fact that the acyl groups are present in different combinations from those observed in natural products. Thus, in the N-acyl-N-lysogangliosides of the invention the acyl groups derive from lower homologues of the fatty acids present in natural products, such as stearic acid, with a maximum of 11 carbon atoms and may also have branched chains. In those derivatives with an acyl group other than acetyl on the neuraminic nitrogen, there may be acyl groups of the aforesaid type on the sphingosine nitrogen or acyls derived from the higher acids typical of natural gangliosides and also homologues with higher molecular weights and up to 24 carbon atoms. In derivatives with free amino groups in their sialic parts there are also lower homologues of "natural" acyls on the sphingosine nitrogen.

Mostly, the acyl-lysogangliosides of the invention are new substances. Some N-acyl-lysoganglioside derivatives have been described which are included in the aforesaid definition, and more precisely:

N,N'-diacetyl-N,N'-di-lyso $GM_1$ (cf. Medical Biology 52, 229–233, 1974)

N-acetyl-N,N'-di-lyso $GM_3$ (Carbohydrate Research 179, 393–410, 1988),

N'-acetyl-N,N'-di-lyso $GM_3$ (Carbohydrate Research 179, 393–410, 1988),

N,N'-diacetyl-N,N'-di-lyso $GM_3$ (Carbohydrate Research 179, 393–410, 1988).

According to the present invention, these compounds, for which no description exists in the literature regarding their pharmacological or therapeutic application, possess the same or analogous pharmacological actions as described hereafter for the new compounds. This application therefore contains claims to the therapeutic use of such substances as well as the pharmaceutical preparations which contain them as active ingredient. The product deacylated both on the neuraminic nitrogen and on the sphingosine nitrogen, described for example in the aforesaid publication in Carbohydrate Research, also possesses similar biological activities and the use of this compound and the pharmaceutical preparations which contain it are also claimed.

The invention also includes the functional derivatives of the sialic carboxy groups of the new acyl-lysogangliosides, that is, esters and amides and also inner esters with lactone bonds between the sialic carboxy groups and the hydroxyls of the oligosaccharide, analogous to those of gangliosides which are already known, as well as the derivatives peracylated on the ganglioside hydroxyls, both of acyl-lysogangliosides and of their aforesaid functional derivatives, and the salts of all the new acyl-di-lysogangliosides and of their functional derivatives.

The main object of the present invention is therefore, more precisely, semisynthetic ganglioside analogues constituted by N-acyl-N,N'-di-lysogangliosides, in which the acyl groups are derived from unsubstituted aliphatic acids with from 1 to 11 carbon atoms, by N'-acyl-N,N'-di-lysogangliosides and N,N'-diacyl-N,N'-di-lysogangliosides, in which the acyl groups are derived from unsubstituted aliphatic acids with from 1 to 24 carbon atoms, but with only 1 to 11 carbon atoms in the case of diacyl derivatives in which the N'-acyl group is acetyl, by the esters and/or amides of their sialic carboxy groups and/or by their inner esters and/or by their peracylated derivatives, and optionally by their metal salts either with organic bases or addition salts with acids, and by mixtures of these compounds, with the exception of N,N'-diacetyl-N,N'-di-lyso $GM_1$, N-acetyl-N,N'-di-lyso $GM_3$, N'-acetyl-N,N'-di-lyso $GM_3$ and N,N'-diacetyl-N,N'-di-lyso $GM_3$.

Another object of the invention is represented by pharmaceutical preparations (compositions) containing one or more of the aforesaid compounds or their mixtures, and/or the corresponding salts, and by pharmaceutical preparations containing as active compound one of the products already described in the literature, or an N-acyl-N,N'-di-lysoganglioside in which the acyl groups are derived from unsubstituted aliphatic acids having from 12 to 24 carbon atoms. A third object is the therapeutic use of the new semisynthetic ganglioside analogues and their aforesaid derivatives, and the use of the aforesaid known products and the aforesaid $N$-acyl-$C_{12-24}$-N,N'-di-lysogangliosides.

A fourth object of the invention is directed to the manufacturing procedures for all of the new aforesaid semisynthetic ganglioside analogues.

The lysogangliosides which serve as a base for the preparation of the new N-acyl derivatives according to the present invention are primarily those which can be obtained by deacylation of gangliosides extractable from natural products, and particularly from tissues of the central or peripheral nervous systems of vertebrates, and also from adrenal marrow, from erythrocytes, from the spleen or other organs. They may be purified gangliosides, as defined in the literature, i.e. those which have a unitary structure in their saccharide part, or they may be ganglioside mixtures.

Among the most important gangliosides to be used as starting base for the new derivatives can be named for example those in which the oligosaccharide is formed by a maximum of 4 hexose residues, and in which this saccharide part is chemically unitary. Hexoses are preferably chosen from the group formed by N-acetylglucosamine and N-acetylgalactoseamine (ganglioside group A). The gangliosides in this group are for example those extracted from vertebrate brain, such as those described in the article "Gangliosides of the Nervous System" in "Glycolipid Methodology", Lloyd A. Witting Ed., American Oil Chemists Society, Champaign, Ill. 187–214 (1976) (see especially Table 1), for example gangliosides $GM_4$, $GM_3$, $GM_2$, $GM1$-GlcNAc, $GD_2$, $GD_{1a}$-GalNAc, $GT_{1c}$, GQ, $GT_1$ and in particular those in which the oligosaccharide contains at least one glucose or galactose residue and one of N-acetylglucosamine or N-acetylgalactoseamine and above all the following (ganglioside group B):

GM$_1$

Gal(1→3)GalNAC(1→4)Gal(1→4)Glc(1→1) Ceramide $$\begin{pmatrix} 3 \\ \uparrow \\ 2 \end{pmatrix}$$
NANA GD$_{1a}$ Gal(1→3)GalNAC(1→4)Gal(1→4)Glc(1→1) Ceramide $$\begin{pmatrix} 3 \\ \uparrow \\ 2 \end{pmatrix} \qquad \begin{pmatrix} 3 \\ \uparrow \\ 2 \end{pmatrix}$$
NANA    NANA GD$_{1b}$ Gal(1→3)GalNAC(1→4)Gal(1→4)Glc(1→1) Ceramide $$\begin{pmatrix} 3 \\ \uparrow \\ 2 \end{pmatrix}$$
NANA $$\begin{pmatrix} 8 \\ \uparrow \\ 2 \end{pmatrix}$$
NANA GT$_{1b}$ Gal(1→3)GalNAC(1→4)Gal(1→4)Glc(1→1) Ceramide $$\begin{pmatrix} 3 \\ \uparrow \\ 2 \end{pmatrix} \qquad \begin{pmatrix} 3 \\ \uparrow \\ 2 \end{pmatrix}$$
NANA    NANA $$\begin{pmatrix} 3 \\ \uparrow \\ 2 \end{pmatrix}$$
NANA where Glc stands for glucose, GalNAC stands for N-acetylgalactosamine, Gal stands for galactose, and NANA stands for N-acetylneuraminic acid. To better illustrate the structure of the gangliosides of the aforesaid formula I, which is substantially the same as for the derivatives of the present invention, and in particular the character of the bond between the saccharide parts, the sialic acids and the ceramide, the following constitutes the complete formula of a "pure" ganglioside GM$_1$ containing one single sialic acid (represented by N-acetylneuraminic or N-glycolylneuraminic acid).

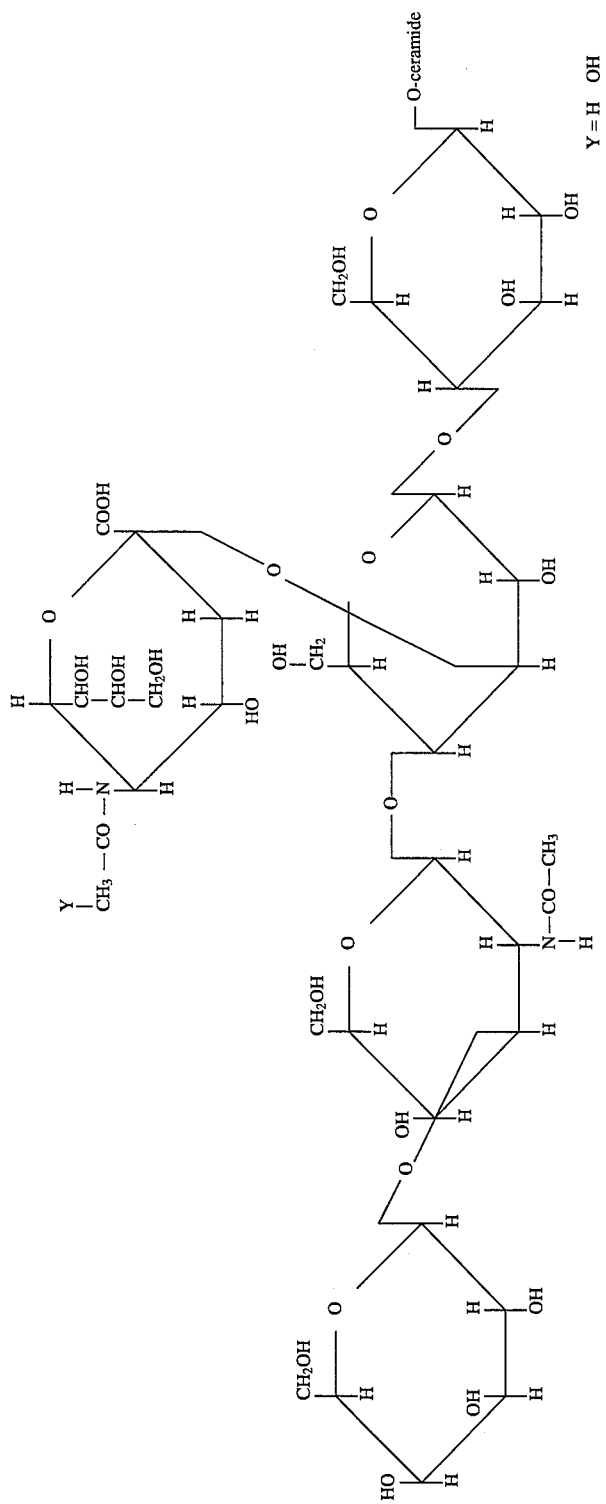

Essentially, the same formula is valid also for a derivative of ganglioside GM$_1$ according to the present invention, with the ceramide residue substituted with a corresponding "artificial" ceramide, in which the N-acyl group is derived from one of the aliphatic acids mentioned previously and/or hereafter, and in which optionally the acetyl group is substituted on the neuraminic nitrogen by one of the acids included in the aforesaid definition of the new compounds.

Included in the present invention are also mixtures of the new N-acyl-lysogangliosides and in particular those which are derived from ganglioside mixtures as present in extracts from various animal tissues, such as in "total" extracts, or in different fractions, for example those described in the literature, for example in the articles quoted above or also in the following articles: "Extraction and analysis of materials containing lipid bound sialic acid" in the aforesaid Witting publication, pages 159–186 (1976) and "Gangliosides of the Nervous System" from the same book, pages 187–214, and German Patent No. 25 49 680. In these new mixtures the N-acyl part of the ganglioside mixtures is substituted with one of the aforesaid acyl groups, and these can be obtained by the procedure of the present invention reported hereafter for the deacylation of these ganglioside mixtures and their subsequent reacylation, optionally, after the reacylation of other deacylated groups in the sialic part of the gangliosides. Among the most important gangliosides to be used as starting products are ganglioside extracts obtained from the nervous system, in particular from the brain and containing gangliosides GM$_1$, GD$_{1a}$, GD$_{1b}$ and GT$_{1b}$ already mentioned.

It is well known that gangliosides play an important role in the nervous system and it has recently been demonstrated that they are useful in therapy for pathologies of the peripheral and central nervous systems [Acta Psychiat. Scand., 55, 102, (1977); Eur. Medicophys., 13, 1, (1977); Ric. Sci. Educ. Perm. Suppl. 9, 115, (1978); Adv. Exp. Med. Biol. 71, 275, (1976); Electromyogr. Clin. Neurophysiol., 19, 353, (1979); Minerva Medica, 69, 3277, (1978); Minerva Stomat., 27, 177, (1978); Med. del Lavoro, 68, 296 (1977); Brain Res. 197, 236, (1980)]. The therapeutic action of gangliosides seems to consist mainly in the stimulation of sprouting phenomena in nerve cells and in activating membrane enzymes involved in nerve conduction, such as the enzyme (Na$^+$,K$^+$) ATPase [Brain Res., 197, 236 (1980), J. of Neurochem. 37, 350 (1981)]. Ganglioside-stimulated neuronal sprouting enhances functional recovery of damaged nerve tissue.

Further studies have been performed to find compounds which may prove more effective than gangliosides in therapy for pathologies of the nervous system. These studies led for example to the discovery that inner esters of gangliosides, in which one or more hydroxyls in the saccharide part are esterified with one or more carboxy groups of the sialic acids (intramolecular reaction) with the formation of the same number of lactone rings, are more active than gangliosides themselves in enhancing neuronal sprouting and in activating the membrane enzymes involved in the conduction of nerve stimuli, such as the enzyme (Na$^+$,K$^+$) ATPase (see for example U.S. Pat. Nos. 4,476,119, 4,593, 091 and 4,716,223).

"Outer" esters of gangliosides also present an improved activity on neuronal sprouting and conduction of nerve stimuli, that is, esters of the carboxy function of sialic acids with various alcohols of the aliphatic, araliphatic, alicyclic and heterocyclic series. Ganglioside amides also possess the same properties, as do the peracylated derivatives of amides, esters and simple gangliosides. All these derivatives, which are described in U.S. Pat. No. 4,713,374, can also be taken as basic substances for the new N-acylated derivatives of the present invention.

The basis of the present invention is the discovery that the new semisynthetic ganglioside analogues described therein and their aforesaid functional derivatives or their salts possess essentially the same pharmacological actions as natural gangliosides or their analogous functional derivatives, with a range of action which is modified in many parameters, such as speed of the "onset", duration and intensity of the sprouting phenomenon of neuronal cells, which may be regulated according to the greater or lesser lipophilic or hydrophilic character of the acyl component, or the type and entity of the side effects, which may in some cases be of a negative or positive kind according to the therapeutic problem being treated, such as above all the inhibiting activity of protein kinase C. In many cases it is possible to use the new derivatives to exploit the particular action of acids corresponding to a given acyl group, disregarding the specific action of the ganglioside part, which in such cases acts primarily as a vehicle. Such is the case, for example, of new compounds according to the invention, in which the N- and N'-acyl groups are derived from an acid which has an action on the central or peripheral nervous system, such as γ-amino-butyric acid.

The new semisynthetic ganglioside analogues of the present invention and those which are already known and have been previously described may therefore be used in place of natural products or their already known semisynthetic derivatives and represent valuable surrogates in cases of patients who do not respond satisfactorily to treatment with conservative products or in cases which present particular idiosyncrasies or allergies. As already noted, they may be used as vehicles because of the specific pharmacological action of the acid corresponding to the acyl groups.

The new ganglioside analogues also possess an inhibiting action on the activation of protein kinase C which may represent an undesirable and negative effect in certain conditions of imbalance of the normal mechanisms of neurotransmitter functions. This activation originates from an increased concentration of excitatory amino acids such as glutamic and/or aspartic acid; these acids, in the aforesaid abnormal conditions, have a direct toxic action on neuronal cells.

A major advantage of the products of the present invention, which sets them apart from other protein kinase C inhibitors, such as gangliosides themselves or sphingosine, consists in their ability to prevent and inhibit the aforesaid neurotoxic action. It is important to emphasize that the products of the present invention, contrary to calcium antagonists and antagonists of glutamate receptors (particularly NMDA), only act under abnormal conditions, limiting localized neurotoxicity and maintaining neuronal plasticity, thereby allowing a more rapid recovery of impaired physiological functions.

The aforesaid pharmacological properties of the new semisynthetic ganglioside analogues can be illustrated by the following experiments conducted on the aforesaid N,N'-diacetyl-N,N'-di-lyso GM$_1$ in comparison to ganglioside GM$_1$ with regard to their capacity to protect from glutamate-induced neurotoxicity in cerebellar granule cells, where possible cytotoxic effects have also been assessed, the neuritogenic effect on neuroblastoma cells and also their capacity to reduce damage caused by ischemia in vivo.

The stimulation of receptors on excitatory amino acids (EAA) can induce translocation of the cytosol membrane and protein kinase (PKC) activation in primary cultures of cerebellar granule cells. This phenomenon probably results from increased $Ca^{+2}$ influx induced by glutamate. It is known that the addition of glutamate to these cells causes cellular damage, presumably mediated by the increased intracellular concentration of $Ca^{+2}$. Exposure of the cerebellar granule cells to gangliosides inhibits the translocation and activation of PKC induced by glutamate.

Furthermore, after acute cerebral ischemia there is a continuous and excessive release of excitatory amino acids (EAA); the continued, prolonged effect of the receptors in the ischemic area induces a cascade of events leading to further degeneration and neuronal death. It is impossible to intervene in atypical events, but it could be possible to limit the phenomena by which ischemia induces the damaged area to spread and increase neuronal death.

Materials and Methods

Experiments in vitro 1.a. Cell culture

Primary cultures of cerebellar granular cells from 8-day-old Sprague-Dawley rats are used on the 11th day of culture. The cultures contain >90% of granule cells, 5% of GABAergic neurons and <5% of glial cells.

1.b. Induction of neurotoxicity by glutamate

Glutamate (50 µM and 100 µM/$Mg^{+2}$ in Locke's solution) is added to the cells and left for 15 min. at room temperature. Controls are without glutamate. The cultures are then washed 3 times with Locke's solution, the solution is removed and the cultures replaced in the original culture medium.

1.c. Solubilization, incubation of the compound and methods of analysis

N,N'-diacetyl-N,N'-di-lyso $GM_1$ was solubilized in Locke's solution at different concentrations (0.3 µM 50 µM) and at different times:

pretreatment: incubated for 15 min., washed 3 times with medium containing serum and then with Locke's solution without $Mg^{+2}$ before the induction of neurotoxicity;

cotreatment: incubated for 15 min. at the same time as 50 µM of glutamate.

Cell survival is assessed 24 hrs later by:

viable cell count by the colorimetric MTT (3-( 4,5-dimethylthiazole-2-yl)-2,5-diphenyl-tetrazolium) method;

viable cell count by the fluorimetric method:

staining of the cultures for 3 min. at 22° C. with a solution containing 36 µM of fluorescent diacetate (FDA) and 7 µM of propidium iodide (PI). The stained cells are immediately examined with a standard fluorescence epi-illumination microscope. Neuronal damage shortens diacetate staining and facilitates penetration of the propidium iodide (polar compound) and interaction with DNA making the complex red and fluorescent. The percentage of surviving cells is counted by measuring the acetate/propridio iodide fluorescence.

2.a. Cell cultures

N2A neuroblastoma cells are seeded at a density of 10,000 cells/well (24-costar) in culture medium composed of DMEM+10% fetal calf serum. 24 hrs after seeding the medium is substituted with 350 µl of fresh medium.

2.b Solubilization and incubation of Ligade 4 and method of analysis

N,N'-diacetyl-N,N'-di-lyso $GM_1$ and $GM_1$ (used as positive control) are dissolved in chloroform/methanol 2:1, dried in $N_2$ current, resuspended in the culture medium and diluted to 50 µM or 100 µM. The cultures are fixed 24 hrs later and morphologically assessed for neuritic growth.

Experiments in vivo

Model: ischemia was induced in newborn rats on the 7th day of life by permanent ligature of the left carotid artery.

The animals were then left to suckle their mothers for 2 hrs in order to recover. They were then placed in an hypoxic chamber (8% di $O_2$) for 2 hrs. This results in cortical damage on the side of the occlusion, characteristically for excitatory amino acids. There is also a reduction in brain weight, and more precisely of the hemisphere on the side of the lesion.

Solubilization, administration of N,N'-diacetyl-N,N'-di-lyso $GM_1$ and parameters examined.

N,N'-diacetyl-N,N'-di-lyso $GM_1$ is solubilized in saline solution and administered at a dose of 10 mg/kg 1 hr before and immediately after damage. The parameter considered was brain weight, taking the controlateral hemisphere as control.

Results

The experiments show that:

N,N'-diacetyl-N,N'-di-lyso $GM_1$ protects (pretreatment for 15 min.) from glutamate-induced neurotoxicity in vitro at concentrations as low as 1 µM with maximum activity (100% protection) at 3–10 µM while 0.3 µM is inactive (FIG. 1).

Activity persists up to 50 µM, demonstrating intrinsic toxicity only at concentrations of >100 µM.

N,N'-diacetyl-N,N'-di-lyso $GM_1$ protects (<100%) from cell death induced by glutamate in vitro even when these are incubated together (cotreatment for 15 mins) (FIG. 2B).

N,N'-diacetyl-N,N'-di-lyso $GM_1$ is active in inducing neuritogenesis on neuroblastoma cells to a greater degree than $GM_1$ (Table 1).

In vivo N,N'-diacetyl-N,N'-di-lyso $GM_1$ administration reduces weight loss of the cerebral hemisphere on the side of the occlusion (Table 2).

Discussion

The results obtained indicate that the ganglioside derivative named N,N'-diacetyl-N,N'-di-lyso $GM_1$ is able to protect from glutamate-induced neurotoxicity and to induce neuritogenesis in vitro and also to diminish brain damage following ischemia in vivo. The biological activity of the new derivative can therefore be considered in those pathologies which are based on damage by glutamate, e.g., cerebral ischemia, trauma, epilepsy, chorea, Parkinson's disease, aging and dementia, cerebral disorders, hypoglycemia and hypoxia.

It should however be noted that some mechanisms at the root of brain damage (release of toxic substances) are also present, for example, in neurocardiovascular damage.

TABLE 1

| Compound | % of neuritic cells |
|---|---|
| Control | 3 + 2% |
| $GM_1$ (100 μM) | 77 + 8% |
| DADL (100 μM) | cell detachment |
| (50 μM) | 83 + 7% |

TABLE 2

Brain weight following hypoxy-ischemic damage in newborn rat

| Treatment | Right Hemisphere | Left Hemisphere | Hemisphere |
|---|---|---|---|
| DADL | 0.394 | 0.271 | −31.22% |
| DADL | 0.390 | 0.360 | −7.69% |
| Saline | 0.398 | 0.296 | −25.63% |
| DADL | 0.417 | 0.386 | −7.43% |
| DADL | 0.419 | 0.377 | −10.02% |
| Saline | 0.404 | 0.317 | −21.53% |
| DADL | 0.416 | 0.302 | −27.40% |
| Saline | 0.420 | 0.245 | −41.67% |
| Saline | 0.407 | 0.286 | −29.61 |
| No. = 3 | 0.007 | 0.021 | 6.14 |
| DADL | 0.407 | 0.339 | −16.75 |
| 10 mg/kg | 0.006 | 0.022 | 5.18 |
| No. = 5 | | | |

Figure 1:
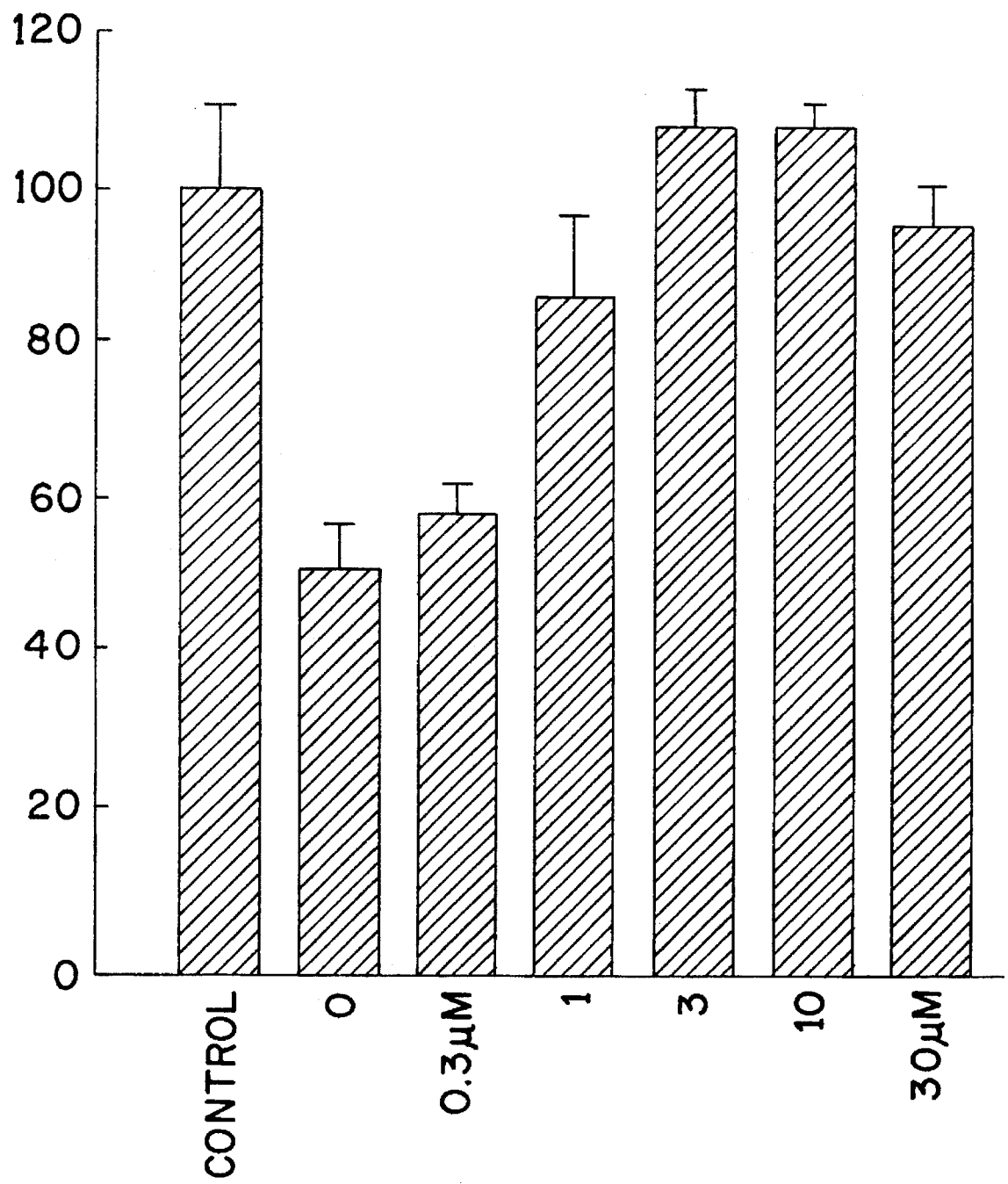
FIG. 1 shows the dose-response of N,N'-diacetyl-N,N'-di-lyso $GM_1$ (DADL) in protecting from glutamate-induced neurotoxicity. The number of surviving cells is assessed by MTT colorimetry (3-(4,5-dimethyl-thiazole- 2-yl)-2,5 diphenyl-tetrazolium).
Figure 2A:
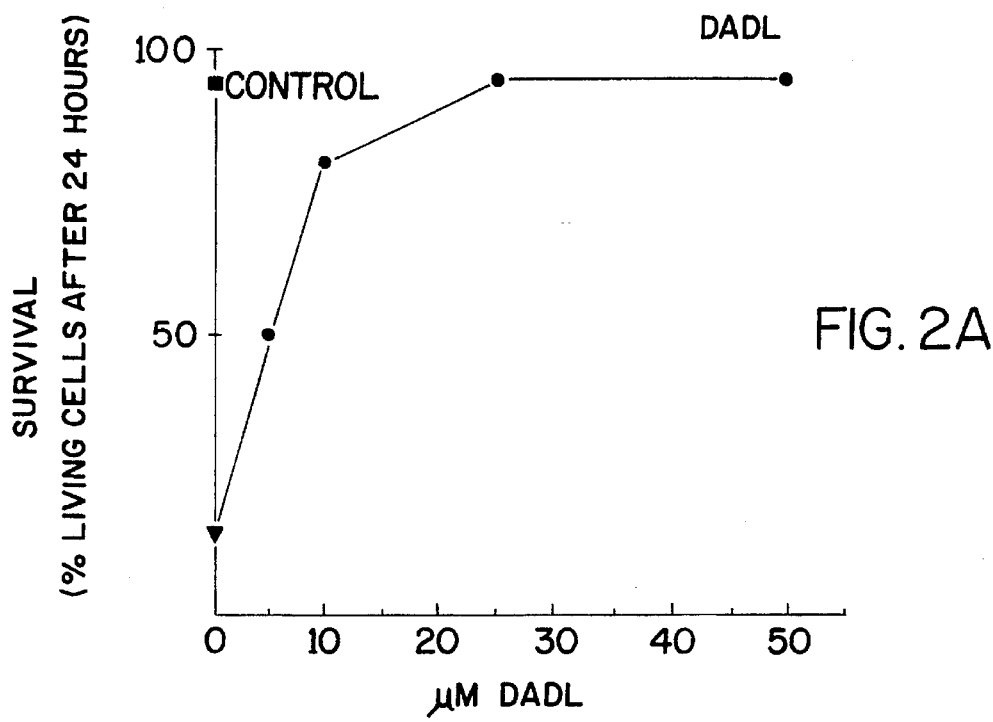
FIG. 2 shows the dose-response of N,N'-diacetyl-N,N'-di-lyso $GM_1$ (DADL) in protecting from glutamate-induced neurotoxicity following 15 minutes of pretreatment (FIG. 2A) and 15 minutes of cotreatment FIG. 2B). Cell survival is assessed by acetate/propidium iodide fluorimetry.
Figure 2B:
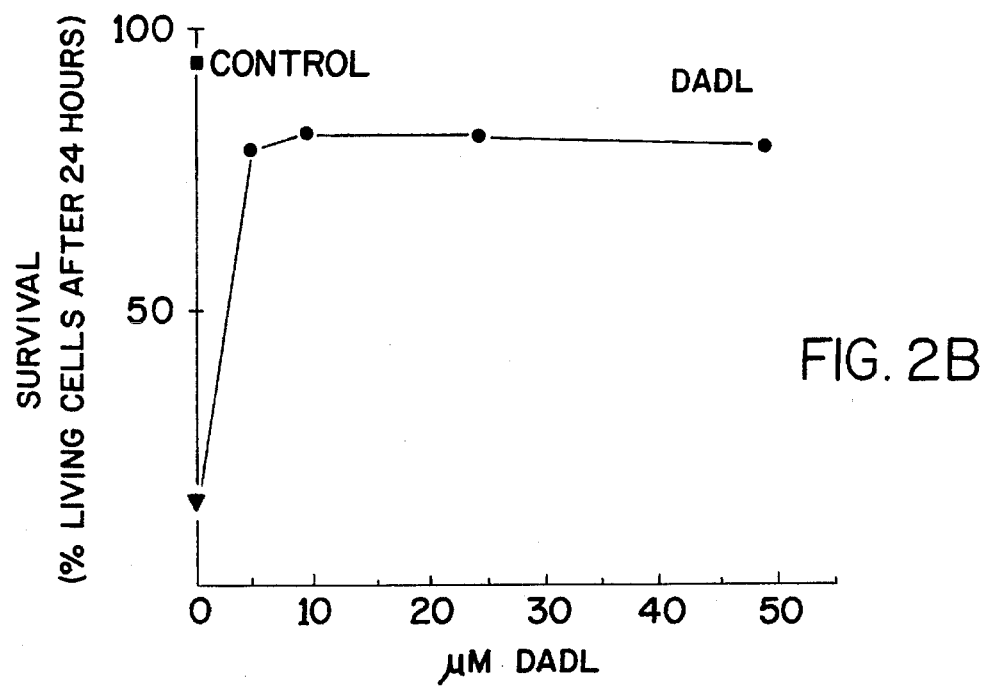

Because of their previously described pharmacological properties, the aforesaid semisynthetic ganglioside analogues can be used as drugs in the following pathologies: cerebral ischemia, metabolic encephalopathies such as hypoglycemia and hypoxia, encephalopathies of toxic origin, trauma, aging, epilepsy, neurodegenerative diseases such as Parkinson's disease and Huntington's chorea, and mental disorders.

Acids with between 1 and 11 carbon atoms from which the acyl groups of the N-acyl-lysogangliosides and N,N'-diacyl-di-lysogangliosides of the present invention are derived, are saturated, with straight or branched chains, for example formic, acetic, propionic, butyric, and valerianic (valeric) acid, such as especially n-valerianic acid, isovalerianic acid, trimethylacetic (pivalic) acid, capronic acid and isocapronic acid, enanthic acid, caprylic acid, pelargonic acid, caprinic acid and undecylic acid, di-tert-butyl-acetic acid and 2-propyl-valerianic acid.

Of the unsaturated acids there can be mentioned angelic acid and tiglic acid.

Of the longer-chained acids with a higher number of carbon atoms, such as up to 24 carbons, special mention must be made of those with straight chains and especially those with between 12 and 16 carbon atoms, for example lauric acid, myristic acid and palmitic acid, and of those with an even higher carbon content such as oleic acid, elaidic acid, stearic acid, eicosacarbonic acid and behenic acid. In the acyl groups with branched chains, both in those with fewer carbon atoms ($C_1$–$C_{11}$), and in those with between 12 and 24 carbon atoms, the lateral chains are preferably lower alkyls with a maximum of 4 carbon atoms, especially methyl groups.

Of the new acyl-lysogangliosides, particularly important are the N,N'-diacyl-di-lysogangliosides, especially those derived from the aforesaid basic gangliosides and from the acids which have received special mention. Some examples thereof are the following:
N,N'-di-formyl-N,N'-di-lyso $GM_1$, N,N'-di-acetyl-di-lyso $GM_1$, N,N-di-propionyl-N,N'-di-lyso $GM_1$,
N,N'-di-butyryl-N,N'-di lyso $GM_1$, N,N'-di-pivaloyl-N,N'-N,N' -di lyso $GM_1$, N,N'-di-valeryl-N,N'-di lyso $GM_1$,
N,N'-di-octanoyl-N,N'-N,N'-di-lyso $GM_1$,
N,N'-di-lauroyl-N,N'-di-lyso $GM_1$,
N,N'-di-2-propyl-pentanoyl-1'N,N'-di-lyso $GM_1$,
N,N'-di-hexanoyl-N,N'-di-lyso $GM_1$,
N,N'-di-isovaleryl-N,N'-di-lyso $GM_1$,
N,N'-di-enantyl-N,N'-di-lyso $GM_1$, N,N'-di-pelargonoyl-N,N' -N,N'-di-lyso $GM_1$, N,N'-di-tert-butyl-acetyl-N,N' -di-lyso $GM_1$, N,N'-di-palmitoyl-N,N' -di-lyso $GM_1$, N,N'-di-lauroyl-N,N-di-lyso $GM_1$,
N,N'-di-stearoyl-N,N'-di-lyso $GM_1$,
N,N'-di-oleyl-N,N'-di-lyso $GM_1$ and analogues derived from the gangliosides $GD_{1a}$, $GD_{1b}$, $GT_{1b}$, $GM_2$ and $GM_3$.

Some examples of derivatives with only one N or N'-acyl group are: N-formyl and N'-formyl-N,N'-di-lyso $GM_1$, N-acetyl and N'-acetyl-N,N'-di-lyso $GM_1$, N-propionyl and N'-propionyl-N,N'-di-lyso $GM_1$, N-butyryl and N'-butyryl-N,N'-di-lyso $GM_1$, N-pivaloyl and N'-pivaloyl-N,N'-di-lyso $GM_1$, N-valeryl and N'-valeryl-N,N'-di-lyso $GM_1$, N-lauroyl and N'-lauroyl-N,N'-di-lyso $GM_1$, N-2-propylpentanoyl and N'-2-propylpentanoyl-N,N'-di-lyso $GM_1$, N-hexanoyl and N'-hexanoyl-N,N'-di-lyso $GM_1$, N-isovaleryl and N'-isovaleryl-N,N'-di-lyso $GM_1$, N-tert-butyl-acetyl and N'-tert-butyl-acetyl-N,N'-di-lyso $GM_1$, N-palmitoyl and N'-palmitoyl-N,N'-di-lyso $GM_1$, N-lauroyl and N'-lauroyl-N,N'-di-lyso $GM_1$, N-stearoyl and N'-stearoyl-N,N'-di-lyso $GM_1$, oleyl and N'-oleyl-N,N' -di-lyso $GM_1$ and analogues derived from the gangliosides $GD_{1a}$, $GD_{1b}$, $GT_{1b}$, $GM_2$ and $GM_3$.

All of the aforesaid derivatives of the new semi-synthetic ganglioside analogues according to the present invention, such as esters, inner esters, amides and peracylates, can be obtained from these compounds by the procedures described in the aforesaid patents for the various corresponding ganglioside derivatives.

The invention also includes mixtures of these derivatives, such as are obtained from mixtures of acyl-lysogangliosides according to the invention, which are in turn obtained from the aforesaid ganglioside mixtures.

The ester groups of the new N-acyl lysoganglioside derivatives are derived particularly from alcohols of the aliphatic series and especially from those with a maximum of 12 and especially 6 carbon atoms, or of the araliphatic series with preferably one single benzene ring, optionally substituted by 1–3 lower alkyl groups ($C_{1-4}$), for example methyl groups, and a maximum of 4 carbon atoms in the aliphatic chain, or by alcohols of the alicyclic or aliphatic alicyclic series with one single cycloaliphatic ring and a maximum of 14 carbon atoms or of the heterocyclic series with a maximum of 12 and especially 6 carbon atoms and one single heterocyclic ring containing a heteroatom chosen from the group formed by N, O and S. The amide groups of the carboxy functions in the N-acyl lysoganglioside derivatives of the present invention are derived from ammonia or from amines of any class with preferably a maximum of 12 carbon atoms.

The aforesaid alcohols and amines can be unsubstituted or substituted, especially by functions chosen from the group formed by hydroxy, amino, alkoxy groups with a maximum of 4 carbon atoms in the alkyl part, carboxy or carbalkoxy groups with a maximum of 4 atoms in the alkyl residue, alkylamino or dialkylamino groups with a maximum of 4 carbon atoms in the alkyl part, and may be saturated or unsaturated, especially with only one double bond. The alcohols which are used to esterify the carboxy functions of the N-acyl lysogangliosides according to the present invention can be monovalent or polyvalent, in particular bivalent. Of the alcohols of the aliphatic series, special mention should be made of lower alcohols with a maximum of 6 carbon atoms, such as methyl alcohol, ethyl alcohol, propyl and isopropyl alcohol, n-butyl alcohol, isobutyl alcohol, and tert-butyl alcohol and of the bivalent alcohols such as ethylene glycol and propylene glycol. Of the alcohols of the araliphatic series special mention should be made of those with one single benzene ring, such as benzyl alcohol and phenethyl alcohol. Alcohols of the alicyclic series are preferably those with one single cycloaliphatic ring, such as cyclohexyl alcohol (cyclohexanol), terpene alcohols such as methanol and carvomenthol, or one of the terpineols or terpineneol or piperitol.

Of the alcohols of the heterocyclic series special mention should be made of tetrahydrofuranol or tetrahydropyranol.

The carboxy groups of the N-acyl lysogangliosides can be esterified with substituted aliphatic alcohols, for example, by amino functions, such as amino-alcohols, for example those with a maximum of 4 carbon atoms and especially amino alcohols with a dialkyl ($C_{1-4}$)-amino group such as diethylaminoethanol.

The carboxyamide functions according to the present invention are either derived from ammonia (the amide in this case being the unsubstituted amide —$CONH_2$) or from primary or secondary amines, especially from those containing a maximum of 12 carbon atoms. These amines can be of an aromatic, heterocyclic, alicyclic, but especially aliphatic nature. A preferred object of the present invention is represented by carboxylamide derivatives of aliphatic amines with a maximum of 12 carbon atoms, and these amines may have open, straight or branched chains and may be cyclic, such as for example alkylamines derived from alkyl groups having from 1 to 6 carbon atoms, such as methylamine or ethylamine, propylamine, hexylamine, dimethylamine, diethylamine, diisopropylamine or dihexylamine, or alkyleneamines derived from alkylene groups with straight chains having from 3 to 6 carbon atoms or corresponding chains substituted by between 1 and 3 methyl groups, such as pyrrolidine, piperidine and azepine. The alkyl or alkylene groups of these amines may also be interrupted in the carbon atom chain or substituted by other hetero-atoms, in particular by nitrogen atoms, and the amides of the invention are derived in this case from diamines, such as for example ethylenediamine, trimethylenediamine and piperazine. When the alkyl or alkylene groups are interrupted or substituted by oxygen or sulfur atoms, the amides are amino alcohol derivatives, such as aminoethanol or aminopropanol or they are derivatives of morpholine or thiomorpholine.

Of special interest to the present invention are the aforesaid esters and amides of N-acyl-lysogangliosides derived from gangliosides of groups A and B mentioned previously, and their mixtures. The invention also includes derivatives, peracylated in the hydroxyls of the saccharide part, of the sialic acids and the ceramide, and of the esters and amides described herein. The acyl groups in these derivatives may be derived from acids of the aliphatic, aromatic, araliphatic, alicyclic or heterocyclic series. They are formed preferably from acids of the aliphatic series with a maximum of 10 carbon atoms and especially 6 carbon atoms, for example formic, acetic, propionic, butyric, valerianic, capronic or caprinic acid. They may also be derived from acids for example with the same number of carbon atoms but substituted, particularly by hydroxyacids such as lactic acid, aminoacids such as glycine or dibasic acids such as succinic, malonic or maleic acids. Of the aromatic acids, those with one single benzene nucleus should be mentioned, particularly benzoic acid and its derivatives with methyl, hydroxyl, amino or carboxy groups, such as p-aminobenzoic acid, salicylic acid or phthalic acid.

The invention also includes peracylated derivatives of N-acyl lysogangliosides and their aforesaid mixtures, but with free carboxy functions. The acylated derivatives of the previously specified acids are also particularly important for these derivatives.

One important group of new derivatives is that constituted by gangliosides which are esterified or converted into amides or peracylated on the hydroxy groups, whose ester groups are derived from aliphatic alcohols with a maximum of 6 carbon atoms, saturated, unsubstituted or substituted by hydroxy or alkoxy groups with a maximum of 4 carbon atoms, amino, alkylamino or dialkylamino groups with a maximum of 4 carbon atoms in the alkyl part, carboxy groups, carbalkoxy groups with a maximum of 4 carbon atoms in the alkyl residue, and by the corresponding unsaturated alcohols with one double bond at the most, by araliphatic alcohols with one single benzene ring, unsubstituted or substituted by between 1 and 3 methyl groups, by cycloaliphatic or aliphatic-cycloaliphatic alcohols with a cyclohexane ring, unsubstituted or substituted by between 1 and 3 methyl groups with a maximum of 4 carbon atoms in the aliphatic part, by tetrahydrofuranol or by tetrahydropyranol. The amide groups in such derivatives are derived from ammonia or from alkylamines, dialkylamines or alkyleneamines with a maximum of 6 carbon atoms in the alkyl group and between 4 and 8 carbon atoms in the alkylene group and in which the alkyl or alkylene groups may be interrupted in the carbon atom chain by heteroatoms chosen from the group formed by nitrogen, oxygen and sulfur, the amino group being perhaps —NH in the case of the presence of a nitrogen atom substituted by an alkyl with a maximum of 4 carbon atoms and/or they may be substituted by groups chosen from the group formed by amino, alkylamino or dialkylamino groups with a maximum of 4 carbon atoms in the alkyl part or by hydroxy or alkoxy groups with a maximum of 4 carbon atoms in the alkyl group, or by araliphatic amines with one single benzene ring optionally substituted by a maximum of 3 methyl groups with a maximum of 4 carbon atoms in the aliphatic part. Acyl groups which esterify the hydroxyls is such derivatives are derived from saturated or unsaturated aliphatic acids with a maximum of 6 carbon atoms, which may also be substituted by a function chosen from the group formed by hydroxy, amino and carbalkoxy groups, and their salts.

It is worth mentioning the following functional derivatives of the new semisynthetic ganglioside analogues, that is, the sialic esters of the aforesaid new compounds, derived from methyl, ethyl, propyl, isopropyl, n-butyl, isobutyl, tert-butyl, benzyl, allyl, ethoxycarbonylmethyl and cyclohexyl alcohols, the sialic amides derived from methylamine, ethylamine, propylamine, dimethylamine, diethylamine, pyrrolidine, piperidine, piperazine, morpholine, thiomorpholine, and the peracylates, perpropionylates, perbutyrylates, permaleylates, persuccinylates and peracylated analogues of the sialic esters and amides mentioned above. Also important are mixtures of acyl-lysogangliosides containing mainly those derived from the gangliosides $GM_1$, $GD_{1a}$, $GD_{1b}$ and $GT_{1b}$ acylated with the aforesaid acids and the functional derivatives analogous to those referred to above for the derivatives of single acyl-lysogangliosides. The semisynthetic ganglioside analogues of the present invention can be prepared in the known way, by acylating the di-lysogangliosides or their N-acyl or N'-acyl derivatives, or optionally by selectively deacylating the N,N'-diacyl-N,N'-di-lysogangliosides on the sphingosine and neuraminic nitrogen.

To prepare di-acyl derivatives in which the acylamino groups are derived from the same acid, it is preferable, for simplicity, to acylate the di-lysogangliosides in a single step by the known methods. Di-lysogangliosides can be obtained from gangliosides or from N-lysogangliosides by alkaline hydrolysis, for example with tetraalkylammonium hydroxides, potassium hydroxide or other alkaline compounds.

To prepare products according to the invention in which the alkylamino groups are derived from different acids, it is preferable to use as starting compounds the N- or N'-monoacyl derivatives of di-lysogangliosides. N-monoacyl-di-lysogangliosides can be obtained by selective acylation from di-lysogangliosides, since the sphingosine amino group is more reactive than the neuraminic amino group. By mildly acylating di-lysogangliosides according to the known methods, for example by the acylation methods used in peptide chemistry, it is possible to obtain the aforesaid monoacyl derivatives on the sphingosine nitrogen. They are then acylated on the neuraminic nitrogen in the conventional manner. The acylation procedure to obtain products according to the invention is comprised, in this case, by a two-step acylation reaction.

If compounds having monoacyl groups on the neuraminic nitrogen are to be used, these can be prepared by various methods. It is possible, for example, to start with di-lysogangliosides and then effect an intermediate provisional protection of the sphingosine amino groups, which can be done for example by hydrophobic interaction with phosphatidylcholine, or by acylation with suitable protective groups, subsequent acylation on the neuraminic nitrogen with a derivative of the acid which is to be introduced into this position, and then deprotection on the sphingosine nitrogen. Lastly, di-lysogangliosides can be acylated on the two amino groups with the same acid and the diacyl compound can be exposed to the action of enzymes which are able to selectively break the acylamino groups alone on the sphingosine nitrogen, for example enzymes used to obtain lysogangliosides from gangliosides, such as the glycosphingolipid-ceramidedeacylase enzyme (see plan 1). N-monoacyl-N,N'-di-lysogangliosides can however also be obtained by deacylating N,N'-diacyl-N,N'-di-lysogangliosides on the neuraminic nitrogen by selective chemical hydrolysis, for example with 0.1 molar alcoholic potassium hydrate.

In the acyl-di-lysogangliosides thus obtained it is possible, if desired, to functionally convert the carboxy groups of the sialic acids or the hydroxyls of these acids, for example to convert them into esters or amides or to convert the hydroxyls in their esterified groups with acids (peracylates).

The procedure for the preparation of N-acyl-N,N'-di-lysogangliosides, in which the acyl groups are derived from unsubstituted aliphatic acids having from 1 to 11 carbon atoms and N'-acyl-N,N'-di-lysogangliosides and N,N'-diacyl-N,N'-di-lysogangliosides, in which the acyl groups are derived from unsubstituted aliphatic acids having from 1 to 24 carbon atoms, but only 1 to 11 carbon atoms in the case of diacyl derivatives in which the N'-acyl group is acetyl (with the exception of N,N'-di-acetyl-N,N'-di-lyso $GM_1$, N-acetyl-N,N'-di-lyso $GM_3$, N'-acetyl-N,N'-di-lyso $GM_3$ and N,N'-di-acetyl-N,N'-di-lyso $GM_3$) comprises acylating N,N'-di-lyso-gangliosides with the acids corresponding to the aforesaid compounds or N-acyl- N,N'-di-lysogangliosides or N'-acyl-di-lysogan- gliosides, or selectively deacylating suitable N,N'-diacyl-N,N'-di-lysogangliosides on the sphingosine or neuraminic nitrogen, or mixtures of these compounds, if desired. The compounds may be converted into esters, amides or inner esters or the compounds obtained may be converted into hydroxy peracylates and, if desired, the products obtained may be converted into salts thereof.

N-acylation according to the aforesaid procedure can be effected in the conventional manner, for example by reacting the starting products with an acylating agent, especially with a functional derivative of the acid, the residue of which is to be introduced. Thus, it is possible to use a halogen or an anhydride as the functional derivative of the acid, and the acylation is carried out preferably in the presence of a tertiary base, such as pyridine or collidine. Anhydrous conditions can be used at room temperature or at higher temperatures, or the Schotten-Baumann method can also be used to advantage, operating in aqueous conditions in the presence of an organic base. In some cases it is also possible to use esters of the acids as reactive functional derivatives. To acylate, it is also possible to use methods with activated carboxy derivatives, such as those used in peptide chemistry, for example the method using mixed anhydrides or derivatives obtainable with carbodiimide derivatives or isoxazole salts. Of all the preparation methods, the following are the most appropriate:

1. reaction of the lysoganglioside derivative with the azide of the acid;
2. reaction of the lysoganglioside derivative with an acylimidazole of the acid obtainable from the acid with N,N'-carbonyldiimidazole;
3. reaction of the lysoganglioside derivative with a mixed anhydride of the acid and of trifluoroacetic acid;
4. reaction of the lysoganglioside derivative with the chloride of the acid;
5. reaction of the lysoganglioside derivative with the acid in the presence of a carbodiimide (such as dicyclohexylcarbodiimide) and optionally a substance such as 1-hydroxybenzotriazole;
6. reaction of the lysoganglioside derivative with the acid by heating;
7. reaction of the lysoganglioside derivative with a methyl ester of the acid at a high temperature;
8. reaction of the lysoganglioside derivative with a phenol ester of the acid, for example an ester with para-nitrophenol;
9. reaction of the lysoganglioside derivative with an ester derived from the exchange between a salt of the acid and 1-methyl-2-chloropyridinium iodide.

It has already been explained how it is possible to obtain selective partial acylation both on the sphingosine and on the neuraminic nitrogen. Scheme 1 illustrates these procedures.

Enzymatic deacylation of N,N'-diacyl-N,N'-di-lysogangliosides on the sphingosine nitrogen as previously reported can be effected under the same conditions as those used for the partial deacylation of gangliosides, for example as described in J. Biochem., 103, 1 (1988). The double deacylation of N,N'-diacyl-N,N'-di-lysogangliosides to N,N'-di-lysogangliosides can be effected in the same way as the preparation of de-N-acetyl-lysogangliosides as described for example in Biochemistry 24, 525 (1985); J. Biol. Chem. 255, 7657, (1980); Biol. Chem. Hoppe Seyler 367, 241, (1986): Carbohydr. Research 179, 393 (1988); Bioch. Bioph. Res. Comn. 147, 127 (1987).

The aforesaid publication in Carbohydr. Research 179 also describes a method for selective deacylation on the neuraminic nitrogen by the action of KOH (0.1M) in 90% normal butanol with the ganglioside $GM_3$. This type of deacylation reaction can be applied to the N,N'-diacyl-N,N'-di-lysogangliosides of the present invention to obtain N-acyl-N,N'-di-lysogangliosides. Of course, all chemical equivalents of this type of preparation method, which would be apparent to one skilled in the art, come within the scope of the present invention.

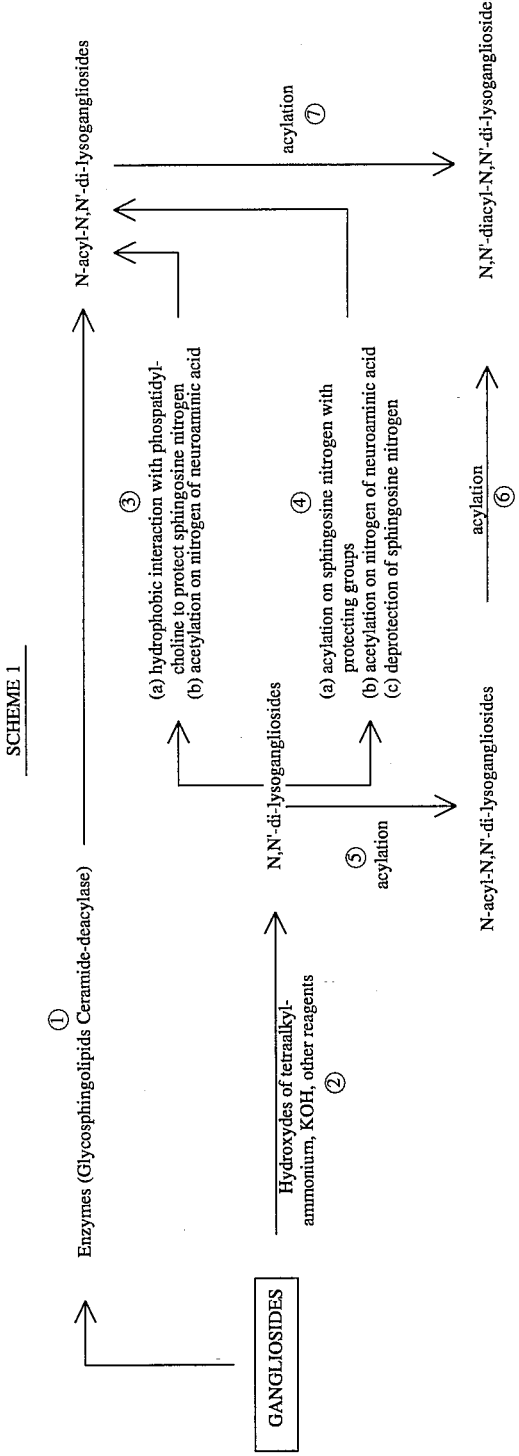

The carboxy or hydroxy derivatives of the new acyl lysogangliosides obtained according to the aforesaid methods, can be prepared according to known procedures, excluding those methods which would have the effect of altering the basic ganglioside structure, such as those involving highly acid agents or which are effected in drastically alkaline or acid conditions, or also those methods which would lead to an undesirable alkylation of the hydroxy groups in the saccharide part. Esterification of the carboxy groups of N-acyl gangliosides or their conversion into amides can be done for example as described in U.S. Pat. No. 4,713,374 for gangliosides. Inner esters of the new derivatives can also be formed in the same way as the inner esters of gangliosides, as described for example in U.S. Pat. No. 4,593,091 and in EP Patent No. 0072722. These inner esters include not only compounds formed by the lactonization of sialic carboxy groups with saccharide hydroxyls, but also for example those containing lactone rings formed between the sialic carboxyls and sialic hydroxyls, since the latter are themselves bound to the saccharide part, and also other possible lactone structures. The procedure of the aforesaid patents for the formation of inner esters comprises treating a ganglioside in a non-aqueous organic solvent under anhydrous conditions with a lactonizing agent. Suitable organic solvents are dimethylsulfoxide, dimethylformamide, sulfolane, tetrahydrofuran, dimethoxyethane, pyridine or mixtures of these solvents. Suitable lactonization reagents include carbodiimides soluble in organic solvents, such as dicyclohexylcarbodiimide, benzylisopropylcarbodiimide, benzylethylcarbodiimide, salts of 2-chloro-1-methylpyridine, ethoxyacetylene and Woodward's reagent (N-ethyl-5-phenylisoxazole-3'-sulfonate). Older methods employ the reaction between a ganglioside and acetic or trichloroacetic acid or with a soluble carbodiimide in water or in an aqueous medium. All of these methods can also be used for the preparation of inner esters of the new N-acyl lysogangliosides of the invention.

For the "outer" esterification of carboxy groups, that is, esterification with alcohols of the aforesaid series, it is possible for example to react the N-acyl lysogangliosides with the desired alcohol, in the presence of an ion exchanger, for example a Dowex 50-type resin, the yield being limited due to the simultaneous formation of inner esters and long reaction times. Another esterification method comprises passing the alcohol over a resin of the type Dowex-50Wx8 (100–200 mesh form H) and treating the eluate dissolved in the same alcohol with the corresponding diazoalkane.

Another good preparation method for esters comprises treating a metal salt of the lysoganglioside derivative with an etherifying agent. Salts of alkaline and alkaline earth metals are used, but also any other metal salt. As an etherifying agent, it is possible to use those mentioned in the literature, especially the esters of various inorganic acids, or organic sulfonic acids, such as hydracids, that is, in other words, hydrocarbyl halogens, such as methyl or ethyl iodide etc., or neutral sulfates or hydrocarbyl acids, sulfites, carbonates, silicates, phosphites or hydrocarbyl sulfonates, for example benzene sulfonate or methyl p-toluenesulfonate. Reaction can be carried out in a suitable solvent, for example an alcohol, preferably an alcohol which corresponds to the alkyl group to be introduced, but also in nonpolar solvents, such as ketones, ethers such as dioxane or dimethylsulfoxide.

One particularly advantageous esterification method comprises treating an inner ester of the lysoganglioside derivative with a mixture of the desired alcohol and its corresponding alcoholate. The reaction can be carried out at a temperature corresponding to the boiling point of the alcohol, however it is also possible to operate at lower temperatures, in which case the reaction times would be longer.

The amides of the lysoganglioside derivatives of the present invention can be prepared by the known methods, especially the following:
a) reaction of inner esters of N-acyl lysoganglioside derivatives with ammonia or amines;
b) reaction of carboxy esters of N-acyl lysoganglioside derivatives with ammonia or amines;
c) reaction of N-acyl lysoganglioside derivatives with activated carboxy groups with ammonia or amines;

Reaction a) can be effected directly, with or without solvent, by treating the ganglioside inner ester with ammonia or with the amine of which the amide is to be prepared. The reaction can also be effected at quite low temperatures, such as from −5° to +10°, but preferably at room temperature or higher, for example between 30° and 120° C. As solvents it is possible to use ketones, aromatic hydrocarbons, dimethylformamide, dimethylsulfoxide, dioxane or tetrahydrofuran.

Reaction b) is effected preferably under the conditions described for a). As well as the esters described for the present invention it is possible to use other esters, for example esters with phenols. In order to activate the carboxy groups in the reaction described in point c), known methods already used in peptide chemistry are used, avoiding procedures which employ excessively acid or basic conditions which would lead to the disintegration of the ganglioside molecule. If the starting gangliosides are in the form of sodium salts it is advisable to first treat the salt with a Dowex-type ion exchange resin or another acid ion exchanger. For example, it is possible to operate by means of condensation in the presence of carbodiimides, for example dicyclohexylcarbodiimide, benzylisopropylcarbodiimide or benzylethylcarbodiimide, in the presence of 1-hydroxybenzotriazole or in the presence of N,N'-carbonyldiimideazole.

Acylation of the hydroxy groups of the saccharide, sialic part and optionally of the ceramide residue can also be effected in the known way, for example by acylation with a halogen or anhydride of the acid used for acylation, preferably in the presence of a tertiary base, such as pyridine or collidine. The above-described peracylated derivatives are thus obtained. It is also possible, according to the definition of the procedure of the present invention, to acylate a de-N-acetyl lysoganglioside and recover the acetylamino group in the neuraminic acid after acylation. This acetylation can be done in the known way. In this case relatively mild methods of N-acylation are chosen, by which the hydroxy group of the neuraminic acid remains unaltered. The acetylation of this group, to be effected after the acylation reaction on the sphingosine nitrogen, can be done by more drastic methods, especially by using acetic anhydride. Lastly, in all the compounds obtainable according to the aforesaid procedures and which present salifiable groups, it is possible to salify such groups in the known way to obtain desired salts of said compounds.

The invention also includes modifications of the preparation procedure of the novel derivatives of the invention, wherein the procedure is interrupted at any one stage or is started from an intermediate compound and the remaining stages are carried out thereafter, or in which the starting products are formed in situ.

The present invention also includes pharmaceutical preparations containing as active substances one or more of the new acyl lyso-ganglioside derivatives and, in particular, those mentioned herein.

The pharmaceutical preparations can be formulations or compositions for oral, rectal, parenteral, local or transdermal use. They are therefore in solid or semisolid form, for example pills, tablets, jelly-like capsules, capsules, suppositories or soft gelatin capsules. For parenteral use it is possible to use pharmaceutical formulations designed for intramuscular, subcutaneous or transdermal administration, or suitable for infusions or intravenous injections, and it is therefore possible for the active compounds to be presented as solutions, or as freeze-dried powders to be mixed with one or more pharmaceutically acceptable excipients or diluents suitable for the aforesaid uses and with osmolarity compatible with physiological fluids. For local use preparations in the form of sprays can be considered, for example nasal sprays, creams or ointments for topical use or suitably prepared plasters for transdermal administration.

The pharmaceutical compositions of the invention can be used for administration to human patients or animals. They contain preferably from 0.01% to 10% by weight of active component in the case of solutions, sprays, ointments and creams and from 1% to 100% by weight and preferably from 5% to 50% by weight of active compound in the case of preparations in solid form. The dosage to be administered depends on the indications in each case, on the desired effect and on the chosen administration route.

Another object of the present invention is represented by the therapeutic use both of the novel acyl-lysogangliosides and of those already known and listed previously. This therapeutic use concerns especially the indications discussed above. The daily dosages to man by an injection route (subcutaneous or intramuscular) or a transdermal or oral route, vary from 0.05 mg to 5 mg of active substance per kg of body weight.

The following Examples illustrate the preparation of the acyl-lysogangliosides of the present invention, pharmaceutical preparations which contain the acyl-lysogangliosides as active ingredients, and therapeutic uses thereof. These Examples are not to be considered as limiting of the present invention.

EXAMPLE 1

N,N'-DI LYSO $GM_1$

Ten (10) gr of $GM_1$ are dissolved in 200 ml KOH 3N and hydrolyzed for 72 hours at 90° C.

The solution is then cooled and brought to pH 6.5 with hydrochloric acid. It is left to rest for 18 hours at 4° C. and then the precipitated fatty acids are eliminated by filtration. It is dialyzed against water and concentrated to 500 ml and precipitated in 5 liters of acetone.

The product is dried and high performance chromatography is effected on silica gel using as eluent a mixture of chloroform/methanol/$NH_3$ 5N (55:45:10). The fractions containing N,N'-di Lyso $GM_1$ are dried and then redissolved in water. It is brought to pH 10 with NaOH 0.01N and dialyzed, concentrated to 100 mg/ml and precipitated in 5 volumes of acetone. Yield of N,N'-di Lyso $GM_1$: 5.7 g (70% theoretical).

After chromatography on a silica gel plate with a solvent of chloroform/methanol/$NH_3$ 5N (55:45:10) the product proves to be a unitary compound with Rf=0.05 ($GM_1$=0.35).

EXAMPLE 2

N,N'-DI-FORMYL-N,N'-DI LYSO $GM_1$ 500 mg (0.39 mM) of N,N'-di Lyso $GM_1$ are dissolved in 2.5 ml of dimethylformamide and 0.88 ml (6.35 mM) of triethylamine, 190 µl (3.17 mM) of formic acid and 0.4 g (1.58 mM) of chloromethylpyridinium iodide dissolved in 2.5 ml of dimethylformamide are added at room temperature.

It is left to react for 18 hrs at room temperature and then precipitated in 100 ml of acetone. It is filtered and dried. The product is then purified by silica gel chromatography using as eluent a mixture of chloroform/methanol/water 60:25:4.

The pure fractions are pooled, evaporated, treated with $Na_2CO_3$ 1N, dialyzed against distilled water and then concentrated to 5 ml and precipitated in 50 ml of acetone.

N,N'-di-formyl-N,N'-di Lyso $GM_1$ is thus obtained: 412 mg (90% theoretical).

Chromatography on silica gel plates with a solvent of chloroform/methanol/$CaCl_2$ 0.3% 60:35:8, shows it to be a unitary compound with Rf=0.27.

EXAMPLE 3

N,N'-DI-ACETYL-N-N'-DI LYSO $GM_1$ 500 mg (0.39 mM) of N,N'-di Lyso $GM_1$ are dissolved in 30 ml of chloroform/methanol/water 1:1:0.1. To the solution are added 104 µl (0.75 mM) of tri-ethylamine and 200 µl (1.80 µM) of acetic anhydride. It is left to react for 2 hrs at room temperature.

At the end of the reaction the product is dried, gathered with 5 ml of chloroform/methanol 1:1 and precipitated in 25 ml of acetone.

The raw product thus obtained (475 mg) is purified by silica gel chromatography using as solvent a mixture of chloroform/methanol/water 60:35:8.

The pure fractions are pooled, evaporated, redissolved in 2.0 ml of chloroform/methanol 1:1 and the product is precipitated in 10 ml of acetone.

N,N'-di-acetyl-N,N'-di Lyso $GM_1$ is thus obtained: 355 mg (85.3% theoretical).

After chromatography on silica gel plates with a solvent of chloroform/methanol/calcium chloride 0.3%, 60:35:8, the product proves to be a unitary compound with Rf=0.29.

EXAMPLE 4

N,N'-DI-PROPIONYL-N-N'-DI LYSO $GM_1$ 500 mg (0.39 mM) of N,N'-di Lyso $GM_1$ are dissolved in 2.5 ml of dimethylformamide/methanol 1:1 and to this are added, at 0° C., 220 µl (1.6 mM) of triethylamine and 204 µl (1.6 mM) of propionic anhydride and it is left to react at room temperature for 168 hrs. It is precipitated in 20 volumes of ethyl acetate, filtered and dried. The product is then purified by silica gel chromatography using as eluent a mixture of chloroform/methanol/water 60:25:4.

The pure fractions are pooled, evaporated, treated with $Na_2CO_3$ 1N, dialyzed against distilled water and then concentrated to 5 ml and precipitated in 50 ml of acetone.

N,N'-di-propionyl-N,N'-di Lyso $GM_1$ is thus obtained: 466 mg (82% theoretical).

Chromatography on silica gel plates with a solvent of chloroform/methanol/$CaCl_2$ 0.3%, 60:35:8, shows it to be a unitary compound with Rf=0.44.

EXAMPLE 5

N,N'-DI-PIVALOYL-N-N'-DI LYSO GM$_1$ 500 mg (0.39 mM) of N,N'-di Lyso GM$_1$ are dissolved in 2.5 ml of dimethylformamide/methanol 1:1 and to this are added at 0° C., 1.1 ml (7.92 mM) of triethylamine and 0.80 ml (3.96 mM) of pivalic anhydride and it is left to react at room temperature for 168 hrs. It is precipitated in 20 volumes of ethyl acetate, filtered and dried.

The product is then purified by silica gel chromatography using as eluent a mixture of chloroform/methanol/water 60:25:4.

The pure fractions are pooled, evaporated, treated with Na$_2$CO$_3$ 1N, dialyzed against distilled water and then concentrated to 5 ml and precipitated in 50 ml of acetone.

N,N'-di-pivaloyl-N,N'-di Lyso GM$_1$ is thus obtained: 436 mg (77% theoretical).

Chromatography on silica gel plates with a solvent of chloroform/methanol/CaCl$_2$ 0.3%, 60:35:8, shows the product to be a unitary compound with Rf=0.57.

EXAMPLE 6

N,N'-DI-TERT-BUTYLACETYL-N,N'-DI LYSO GM$_1$ 500 mg (0.39 mM) of N,N'-di Lyso GM$_1$ are dissolved in 2.5 ml of dimethylformamide and to this are added at room temperature 0.33 ml (2.37 mM) of triethylamine, 165 µl (1.18 mM) of tert-butyl acetic acid and 0.2 g (0.79 mM) of chloromethylpyridinium iodide dissolved in 2.5 ml of dimethylformamide.

It is left to react for 18 hrs at room temperature and then precipitated in 100 ml of acetone. It is filtered and dried. The product is then purified by silica gel chromatography using as eluent a mixture of chloroform/methanol/water 60:25:4.

The pure fractions are pooled, evaporated, treated with Na$_2$CO$_3$ 1N, dialyzed against distilled water and then concentrated to 5 ml and precipitated in 50 ml of acetone.

N,N'-di-tert-butylacetyl-N,N'-di Lyso GM$_1$ is thus obtained: 289 mg (50% theoretical).

Chromatography on silica gel plates with a solvent of chloroform/methanol/CaCl$_2$ 0.3%, 60:35:8, shows the product to be a unitary compound with Rf=0.30.

EXAMPLE 7

N,N'-DI-(2-PROPYLPENTANOYL)-N,N'-DI LYSO GM$_1$ 500 mg (0.39 mM) of N,N'-di Lyso GM$_1$ are dissolved in 2.5 ml of dimethylformamide and to this are added at room temperature 0.33 ml (2.37 mM) of triethylamine, 186 µl (1.18 mM) of 2-propylpentanoic acid and 0.2 g (0.79 mM) of chloromethylpyridinium iodide dissolved in 2.5 ml of dimethylformamide.

It is left to react for 18 hrs at room temperature and then precipitated in 100 ml of acetone. It is filtered and dried. The product is then purified by silica gel chromatography using as eluent a mixture of chloroform/methanol/water 60:25:4.

The pure fractions are pooled, evaporated, treated with Na$_2$CO$_3$ 1N, dialyzed against distilled water and then concentrated to 5 ml and precipitated in 50 ml of acetone.

N,N'-di-(2-propylpentanoyl)-N,N'-di Lyso GM$_1$ is thus obtained: 570 mg (95% theoretical).

Chromatography on silica gel plates with a solvent of chloroform/methanol/CaCl$_2$ 0.3%, 60:35:8, shows the product to be a unitary compound with Rf=0.32.

EXAMPLE 8

N-ACETYL-N,N'-DI LYSO GM$_1$ 500 mg of N,N'-di Lyso GM$_1$ (0.39 mM) are dissolved in 5 ml of dimethylformamide; to this solution are slowly added 145 mg (0.43 mM) of 9-fluorenyl-methyloxy-carbonyl-N-hydroxysuccinimide (FMOC-succ.) and it is left to react for 1 hr at room temperature.

When reaction is complete it is precipitated in 100 ml of acetone, filtered and dried. The product is then purified by silica gel chromatography using as solvent a mixture of chloroform/methanol/water 60:30:6.

The fractions containing the intermediate product N-FMOC-N,N'-di Lyso GM$_1$ are pooled, dried and redissolved in 2.5 ml of dimethylformamide/methanol 1:1 and to this are added, at 0° C., 1.1 ml (7.92 mM) of triethylamine and 0.40 ml (3.96 mM) of methyl tri-fluoroacetate and it is left to react at room temperature for 3 days.

1 ml of piperidine is then added to remove the fluorenyl group. It is left to react for 18 hrs at room temperature and it is precipitated in 100 ml of acetone/water 9:1, filtered and dried.

The intermediate product is dissolved in 30 ml of chloroform/methanol/water 1:10.1 and to this are added 250 µl (1.80 mM) of triethylamine and 100 µl (0.90 mM) of acetic anhydride. It is left to react for 2 hrs at room temperature, dried, redissolved in 5 ml of water and brought to pH 9.0 with NaOH 0.01N. It is left at room temperature to remove the trifluoroacetyl group. It is dialyzed, concentrated to 3 ml and precipitated in 15 ml of acetone.

The raw product thus obtained is purified by silica gel chromatography using as eluent a mixture of chloroform/methanol/water 60:35:8.

The pure fractions are pooled, evaporated, redissolved in 2.0 ml of chloroform/methanol 1:1 and precipitated in 10 ml of acetone.

N-acetyl-N,N'-di Lyso GM$_1$ is thus obtained: 243.8 mg (48% theoretical).

Chromatography on silica gel plates with a solvent of chloroform/methanol/CaCl$_2$ 0.3% 50:42:11, shows the product to be a unitary compound with Rf=0.12 and positive to ninhydrin staining.

EXAMPLE 9

N-ACETYL-N'-BUTYRL-N,N'-DI LYSO GM$_1$ 500 mg of N,N'-di Lyso GM$_1$ (0.39 mM) are dissolved in 5 ml of dimethylformamide; to this solution are slowly added 145 mg (0.43 mM) of 9-fluorenyl-methyloxy-carbonyl-N-hydroxysuccinimide (FMOC-succ.) and it is left to react for 1 hr at room temperature.

When the reaction is complete, it is precipitated in 100 ml of acetone, filtered and dried. The product is then purified by silica gel chromatography using as solvent a mixture of chloroform/methanol/water 60:30:6.

The fractions containing the intermediate product (N-FMOC-N,N'-di Lyso GM$_1$) are pooled, dried and redissolved in 2.5 ml of dimethylformamide/methanol 1:1 and to this are added, at 0° C., 1.1 ml (7.92 mM) of triethylamine and 626 mg (3.96 mM) of butyric anhydride.

To this reaction mixture is then added 1 ml of piperidine to remove the fluorenyl group. It is left to react for 18 hrs at room temperature and it is precipitated in 100 ml of acetone/water 9:1, filtered and dried.

The intermediate product is dissolved in 30 ml of chloroform/methanol/water 1:1; 0.1 and to this are added 1.1 ml (7.92 ml) of triethylamine and 373 μl (3.96 mM) of acetic anhydride. It is left to react for 2 hrs at room temperature, dried, redissolved in 5 ml of $Na_2CO_3$ 1M and kept at 60° C. for 1 hr. It is dialyzed, concentrated to 5 ml and precipitated in 5 volumes of acetone.

The raw product of the reaction is purified by silica gel chromatography using as solvent a mixture of chloroform/methanol 60:35:8.

The pure fractions are pooled, evaporated, redissolved in 2.0 ml of chloroform/methanol 1:1 and precipitated in 10 ml of acetone.

N-acetyl-N'-butyrl-N,N'-di Lyso $GM_1$ is thus obtained: 278 mg (52% theoretical).

Chromatography on silica gel plates with a solvent of chloroform/methanol/$CaCl_2$ 0.3% 50:42:11, shows the product to be a unitary compound with Rf=0.32.

EXAMPLE 10

N-ACETYL-N'-LAUROYL-N,N'-DI LYSO $GM_1$ 500 mg of N,N'-di Lyso $GM_1$ (0.39 mM) are dissolved in 5 ml of dimethylformamide; to this solution are slowly added 145 mg (0.43 mM) of 9-fluorenyl-methyloxy-carbonyl-N-hydroxysuccinimide (FMOC-succ.) and it is left to react for 1 hr at room temperature.

When the reaction is complete it is precipitated in 100 ml of acetone, filtered and dried. The product is then purified by silica gel chromatography using as solvent a mixture of chloroform/methanol/water 60:30:6.

The fractions containing the intermediate product (N-FMOC-N,N'-di Lyso $GM_1$) are pooled, dried and redissolved in 2.5 ml of dimethylformamide/methanol 1:1 and to this are added, at 0° C., 1.1 ml (7.92 mM) of triethylamine and 1.51 g (3.96 mM) of lauric anhydride and it is left to react at room temperature for 18 hrs.

To this reaction mixture is then added 1 ml of piperidine to remove the fluorenyl group. It is left to react for 18 hrs at room temperature and precipitated in 100 ml of acetone/water 9:1, filtered and dried.

The intermediate product is dissolved in 30 ml of chloroform/methanol/water 1:1; 0.1 and to this are added 1.1 ml (7.92 ml) of triethylamine and 373 μl (3.96 mM) of acetic anhydride. It is left to react for 2 hours at room temperature, dried, redissolved in 5 ml of $Na_2CO_3$ 1M and kept at 60° C. for 1 hr. It is dialyzed, concentrated to 5 ml and precipitated in 5 volumes of acetone.

The raw product of the reaction is purified by silica gel chromatography using as solvent a mixture of chloroform/methanol/water 60:35:8.

The pure fractions are pooled, evaporated, redissolved in 2.0 ml of chloroform/methanol 1:1 and precipitated in 10 ml of acetone.

N-acetyl-N'-lauroyl-N,N'-di Lyso $GM_1$ is thus obtained: 295 mg (51% theoretical).

Chromatography on silica gel plates with a solvent of chloroform/methanol/$CaCl_2$ 0.3% 50:42:11, shows the product to be a unitary compound with Rf=0.55.

EXAMPLE 11

N'-ACETYL-N,N'-DI LYSO $GM_1$ 10 g (6.37 mM) of $GM_1$ are dissolved in 200 ml of KOH 3N and hydrolyzed for 72 hours at 90° C.

The solution is then cooled and brought to pH 6.5 with hydrochloric acid. It is left to rest for 18 hours at 4° and then the precipitated fatty acids are eliminated by filtration. It is dialyzed against water and concentrated to 500 ml and precipitated in 5 liters of acetone.

The product is vacuum dried and then redissolved in 100 ml of dimethylformamide.

To this are then slowly added 2.15 g (6.37 MM) of 9-fluorenyl-methyloxycarbonyl-N-hydroxysuccinimide dissolved in 20 ml of tetrahydrofuran and it is left to react for 1 hr at room temperature. After this are added 3 ml (31.85 μM) of acetic anhydride and 0.09 ml (6.37 mM) of triethylamine.

30 minutes later 12.5 ml of piperidine are added to remove the protecting group. It is left to react for 18 hrs at room temperature and then precipitated in 2 liters (lt) of acetone and dried. The material thus obtained is dissolved in $Na_2CO_3$ 1M and kept at 60° C. for 1 hr. It is dialyzed, concentrated to 100 mg/ml and precipitated in 5 volumes of acetone.

The product is passed through an S-Sepharose column ($H^+$ form) equilibrated with methanol. It is eluted with methanol, thus obtaining the N'-acetyl-N,N'- derivative of Lyso $GM_1$ eluting with $NH_4Cl$ 10 mM in methanol. The fractions containing the product are dried and then redissolved in water. The are brought to pH 10 with NaOH 0.01N and dialyzed, concentrated to 100 mg/ml and precipitated in 5 volumes of acetone. N'-acetyl-N,N'-di Lyso $GM_1$ is thus obtained: 5 g (60% theoretical).

Chromatography on silica gel plates with a solvent of chloroform/methanol/$NH_3$ 5N, 55:45:10, shows the product to be unitary with Rf=0.11.

EXAMPLE 12

N'-PROPIONYL-N,N'-DI LYSO $GM_1$ 500 mg of N,N'-di Lyso $GM_1$ (0.39 mM) are dissolved in 5 ml of dimethylformamide; to this solution are slowly added 145 mg (0.43 mM) of 9-fluorenyl-methyloxy-carbonyl-N-hydroxysuccinimide dissolved in 2 ml of tetrahydrofuran and it is left to react for 1 hr at room temperature.

After reaction, 253.7 mg (1.95 mM) of n-propionic anhydride and 54.5 μl (0.39 mM) of triethylamine are added.

30 minutes later 2 ml of piperidine are added to remove the protecting group. It is left to react for 18 hrs at room temperature and precipitated in 100 ml of acetone. It is filtered and dried. The product thus obtained is dissolved in 10 ml of $Na_2CO_3$ 1M and kept at 60° C. for 1 hr. It is dialyzed, concentrated to 5 ml and precipitated in 5 volumes of acetone.

The raw product of the reaction is purified by silica gel chromatography using as solvent a mixture of chloroform/methanol/$NH_3$ 2.5N 60:35:8. The fractions containing the pure product are dried and then redissolved in 5 ml of water. It is brought to pH 10 with NaOH 0.01N and dialyzed, concentrated to 5 ml and precipitated in 5 ml of acetone.

N'-propionyl-N,N'-di Lyso $GM_1$ is thus obtained: 310 mg (60.4% theoretical).

Chromatography on silica gel plates with a solvent of chloroform/methanol/CaCl$_2$ 0.3% 50:42:11, shows the product to be a unitary compound with Rf=0.27 and positive to ninhydrin staining.

EXAMPLE 13

N-FORMYL-N'-ACETYL-DI LYSO GM$_1$ 500 mg (0.38 mM) of N'-acetyl-N,N'-di Lyso GM$_1$ are dissolved in 2.5 ml of dimethylformamide and to this are added at room temperature 1056 μl (7.6 mM) of triethylamine, 237 μl (3.8 mM) of formic acid and 194.2 mg (0.76 mM) of chloromethylpyridinium iodide dissolved in 2.5 ml of dimethylformamide.

It is left to react for 18 hrs at room temperature and then precipitated in 100 ml of acetone. It is filtered and dried. The product is then purified by silica gel chromatography using as eluent a mixture of chloroform/methanol/water 60:30:6.

The pure fractions are pooled, evaporated, treated with Na$_2$CO$_3$ 1N, dialyzed against distilled water and then concentrated to 5 ml and precipitated in 50 ml of acetone.

N-formyl-N'-acetyl-di Lyso GM$_1$ is thus obtained: 391 mg (75% theoretical).

Chromatography on silica gel plates with a solvent of chloroform/methanol/CaCl$_2$ 0.3% 60:35:8, shows the product to be a unitary compound with Rf=0.27.

EXAMPLE 14

N-PROPIONYL-N'-ACETYL-DI LYSO GM$_1$ 500 mg (0.38 mM) of N'-acetyl-N,N'-di Lyso GM$_1$ are dissolved in 5 ml of dimethylformamide/methanol 1:1 and to this are added at 0° C., 422 μl (3.04 mM) of triethylamine and 196 μl (1.52 mM) of propionic anhydride and it is left to react at room temperature for 72 hrs. It is precipitated in 20 volumes of ethyl acetate, filtered and dried.

The product is then purified by silica gel chromatography using as eluent a mixture of chloroform/methanol/water 60:35:8.

The pure fractions are pooled, evaporated, treated with Na$_2$CO$_3$ 1N, dialyzed against distilled water and then concentrated to 5 ml and precipitated in 50 ml of acetone.

N-propionyl-N'-acetyl-di Lyso GM$_1$ is thus obtained: 522 mg (70.0% theoretical).

Chromatography on silica gel plates with a solvent of chloroform/methanol/CaCl$_2$ 0.3% 60:35:8, shows the product to be unitary with Rf=0.31.

EXAMPLE 15

N-BUTYRYL-N'-ACETYL-DI LYSO GM$_1$ 500 mg (0.38 mM) of N'-acetyl-N,N'-di Lyso GM$_1$ are dissolved in 5 ml of dimethylformamide/methanol 1:1 and to this are added at 0° C., 422 μl (3.04 mM) of triethylamine and 249 μl (1.52 mM) of butyric anhydride and it is left to react at room temperature for 72 hrs. It is precipitated in 20 volumes of ethyl acetate, filtered and dried.

The product is then purified by silica gel chromatography using as eluent a mixture of chloroform/methanol/water 60:35:8.

The pure fractions are pooled, evaporated, treated with Na$_2$CO$_3$ 1N, dialyzed against distilled water and then concentrated to 5 ml and precipitated in 50 ml of acetone.

N-butyryl-N'-acetyl-di Lyso GM$_1$ is thus obtained: 527 mg (68.0% theoretical).

Chromatography on silica gel plates with a solvent of chloroform/methanol/CaCl$_2$ 0.3% 60:35:8, shows the product to be unitary with Rf=0.32.

EXAMPLE 16

N-PIVALOYL-N'-ACETYL-DI LYSO GM$_1$ 500 mg (0.38 mM) of N'-acetyl-N,N'-di Lyso GM$_1$ are dissolved in 5 ml of dimethylformamide/methanol 1:1 and to this are added at 0° C., 528 μl (3.8 mM) of triethylamine and 780 μl (3.8 mM) of pivalic anhydride and it is left to react at room temperature for 72 hrs. It is precipitated in 20 volumes of ethyl acetate, filtered and dried.

The product is then purified by silica gel chromatography using as eluent a mixture of chloroform/methanol/water 60:35:8.

The pure fractions are pooled, evaporated, treated with Na$_2$CO$_3$ 1N, dialyzed against distilled water and then concentrated to 5 ml and precipitated in 50 ml of acetone.

N-pivaloyl-N'-acetyl-di Lyso GM$_1$ is thus obtained: 490 mg (94.0% theoretical).

Chromatography on silica gel plates with a solvent of chloroform/methanol/CaCl$_2$ 0.2% 50:42:11, shows the product to be unitary with Rf=0.34.

EXAMPLE 17

N-HEXANOYL-N'-ACETYL-DI LYSO GM$_1$ 500 mg (0.38 mM) of N'-acetyl-N,N'-di Lyso GM$_1$ are dissolved in 2.5 ml of dimethylformamide and to this are added at room temperature 316 μl (2.28 mM) of triethylamine, 143 μl (1.14 mM) of hexanoic acid and 194.2 mg (0.76 mM) of chloromethylpyridinium iodide dissolved in 2.5 ml of dimethylformamide.

It is left to react for 18 hrs at room temperature and then precipitated in 100 ml of acetone. It is filtered and dried. The product is then purified by silica gel chromatography using as eluent a mixture of chloroform/methanol/water 60:30:6.

The pure fractions are pooled, evaporated, treated with Na$_2$CO$_3$ 1N, dialyzed against distilled water and then concentrated to 5 ml and precipitated in 50 ml of acetone.

N-hexanoyl-N'-acetyl-di Lyso GM$_1$ is thus obtained: 392 mg (73% theoretical).

Chromatography on silica gel plates with a solvent of chloroform/methanol/CaCl$_2$ 0.3% 60:35:8, shows the product to be a unitary compound with Rf=0.33.

EXAMPLE 18

N-(2-PROPYLPENTANOYL)-N'-ACETYL-DI LYSO GM$_1$ 500 mg (0.38 mM) of N'-acetyl-N,N'-di Lyso GM$_1$ are dissolved in 2.5 ml of dimethylformamide and to this are added at room temperature 1056 μl (7.6 mM) of triethylamine, 595 μl (3.8 mM) of 2-propyl-pentanoic acid and 194.2 mg (0.76 mM) of chloro-methylpyridinium iodide dissolved in 2.5 ml of dimethylformamide.

It is left to react for 18 hrs at room temperature and then precipitated in 100 ml of acetone. It is filtered and dried. The product is then purified by silica gel chromatography using as eluent a mixture of chloroform/methanol/water 60:30:6.

The pure fractions are pooled, evaporated, treated with Na$_2$CO$_3$ 1N, dialyzed against distilled water and then concentrated to 5 ml and precipitated in 50 ml of acetone.

N-(2-propylpentanoyl)-N'-acetyl-di Lyso GM$_1$ is thus obtained: 428 mg (75% theoretical).

Chromatography on silica gel plates with a solvent of chloroform/methanol/CaCl$_2$ 0.3% 60:35:8, shows the product to be a unitary compound with Rf=0.35.

EXAMPLE 19

N-OCTANOYL-N'-ACETYL-DI-LYSO GM$_1$ 500 mg (0.38 mM) of N'-acetyl-N,N'-di Lyso GM$_1$ are dissolved in 2.5 ml of dimethylformamide and to this are added at room temperature 316 μl (2.28 mM) of triethylamine, 181 μl (1.14 mM) of octanoic acid and 194.2 mg (0.76 mM) of chloromethylpyridinium iodide dissolved in 2.5 ml of dimethylformamide.

It is left to react for 18 hrs at room temperature and then precipitated in 100 ml of acetone. It is filtered and dried. The product is then purified by silica gel chromatography using as eluent a mixture of chloroform/methanol/water 60:30:6.

The pure fractions are pooled, evaporated, treated with Na$_2$CO$_3$ 1N, dialyzed against distilled water and then concentrated to 5 ml and precipitated in 50 ml of acetone.

N-octanoyl-N'-acetyl-di Lyso GM$_1$ is thus obtained: 427 mg (78% theoretical).

Chromatography on silica gel plates with a solvent of chloroform/methanol/CaCl$_2$ 0.3% 60:35:8, shows the product to be a unitary compound with Rf=0.34.

EXAMPLE 20

N-LAUROYL-N'-ACETYL-DI LYSO GM$_1$ 500 mg (0.38 mM) of N'-acetyl-N,N'-di Lyso GM$_1$ are dissolved in 2.5 ml of dimethylformamide and to this are added at room temperature 316 μl (2.28 mM) of triethylamine, 152 mg (1.14 mM) of lauric acid and 194.2 mg (0.76 mM) of chloromethylpyridinium iodide dissolved in 2.5 ml of dimethylformamide.

It is left to react for 18 hrs at room temperature and then precipitated in 100 ml of acetone. It is filtered and dried. The product is then purified by silica gel chromatography using as eluent a mixture of chloroform/methanol/water 60:30:6.

The pure fractions are pooled, evaporated, treated with Na$_2$CO$_3$ 1N, dialyzed against distilled water and then concentrated to 5 ml and precipitated in 50 ml of acetone.

N-lauroyl-N'-acetyl-di Lyso GM$_1$ is thus obtained: 353 mg (62% theoretical).

Chromatography on silica gel plates with a solvent of chloroform/methanol/CaCl$_2$ 0.3% 60:35:8, shows the product to be a unitary compound with Rf=0.37.

EXAMPLE 21

N-DECANOYL-N'-ACETYL-DI LYSO GM$_1$ 500 mg (0.39 mM) of N,N'-di Lyso GM$_1$ are dissolved in 5 ml of dimethylformamide and to this are added 1 ml of Triton X 100 and 104 μl (0.75 mM) of tri-ethylamine. This is stirred until a clear solution is obtained. To this are then added 25 ml of tetrahydrofuran containing 380 mg (1.5 mM) of the N-succinimidyl derivative of decanoic acid prepared by reaction for 18 hrs at room temperature, 500 mg (2.9 mM) of decanoic acid dissolved in 15 ml of anhydrous tetrahydrofuran with 742 mg (2.9 mM) of N-succinimidyl carbonate and 550 μl (43.9 mM) of triethylamine in 40 ml of acetone.

Reaction is conducted for 24 hrs at room temperature after which the solution is concentrated to 5 ml and precipitated in 100 ml of acetone.

The raw product thus obtained is purified by silica gel chromatography using as solvent a mixture of chloroform/methanol/water 60:30:6.

The pure fractions are pooled, evaporated, redissolved in 2 ml of chloroform/methanol 1/1 and to this are then added 73.5 μl (0.78 mM) of acetic anhydride and 108 μl (0.78 mM) of triethylamine. It is left to react at room temperature for 24 hrs and then precipitated in 100 ml of acetone.

The product is then purified by further silica gel chromatography using as solvent a mixture of chloroform/methanol/water 60:35:8. The pure fractions are pooled, evaporated, treated with Na$_2$CO$_3$ 1N, dialyzed against distilled H$_2$O, concentrated to 5 ml and precipitated in 100 ml of acetone.

N-decanoyl-N'-acetyl-di Lyso GM$_1$ is thus obtained: 184 mg (32% theoretical).

Chromatography on silica gel plates with a solvent of chloroform/methanol/calcium chloride 0.3%, 60:35:8 shows the product to be a unitary compound with Rf= 0.34.

EXAMPLE 22

N-MYRISTOYL-N'-ACETYL-DI LYSO GM$_1$ 500 mg (0.39 mM) of N,N'-di Lyso GM$_1$ are dissolved in 5 ml of dimethylformamide and to this are added 1 ml of Triton X 100 and 104 μl (0.75 mM) of tri-ethylamine. This is stirred until a clear solution is obtained. To this solution are then added 25 ml of tetra-hydrofuran containing 380 mg (1.5 mM) of the N-succinimidyl derivative of myristic acid prepared by reaction for 18 hrs at room temperature, 500 mg (2.2 mM) of myristic acid dissolved in 15 ml of anhydrous tetrahydrofuran with 742 mg (2.9 mM) of N-succinimidylcarbonate and 550 μl (43.9 mM) of triethylamine in 40 ml of acetone.

Reaction is conducted for 24 hrs at room temperature after which the solution is concentrated to 5 ml and precipitated in 100 ml of acetone.

The raw product thus obtained is purified by silica gel chromatography using as solvent a mixture of chloroform/methanol/water 60:30:6.

The pure fractions are pooled, evaporated, and redissolved in 2 ml of chloroform/methanol 1/1, and to this are then added 73.5 μl (0.78 mM) of acetic anhydride and 108 μl (0.78 mM) of triethylamine. Reaction is carried out at room temperature for 24 hrs, and then the reaction mixture is precipitated in 100 ml of acetone.

The product is then purified by further silica gel chromatography using as solvent a mixture of chloroform/methanol/water 60:35:8. The pure fractions are pooled, evaporated, treated with Na$_2$CO$_3$ 1N, dialyzed against distilled H$_2$O, concentrated to 5 ml and precipitated in 100 ml of acetone.

N-myristoyl-N'-acetyl-di Lyso GM$_1$ is thus obtained: 210 mg (35% theoretical). Chromatography on silica gel plates with a solvent of chloroform/methanol/calcium chloride 0.3%, 60:35:8, shows the product to be a unitary compound with Rf=0.38.

EXAMPLE 23

NATURAL N'-LYSO $GM_1$ 500 mg (0.31 mM) of $GM_1$ are dissolved in 50 ml of sodium hydrate 1N. The reaction mixture is then kept at a temperature of 90° C. for 18 hrs. The solution thus obtained is dialyzed, concentrated to 2.5 ml and precipitated in 100 ml of acetone.

The raw product thus obtained is purified by silica gel chromatography using as eluent a mixture of chloroform/methanol/$H_2O$ 60:30:6.

The pure fractions are pooled, evaporated, redissolved in 2.5 ml of chloroform/methanol 1:1 and precipitated in 100 ml of acetone.

Natural N'-lyso $GM_1$ is thus obtained: 350 mg (72% theoretical).

Chromatography on silica gel plates with a solvent of chloroform/methanol/$CaCl_2$ 0.3% 60:35:8, shows Rf= 0.20.

The fatty acid content, bound on the sphingosine nitrogen with an amide bond, proved to be: 95% stearic acid, 4% oleic acid, 0.5% palmitic acid, 0.5% other fatty acids. Determination was made by gas chromatography of the methyl esters of the fatty acids obtained by esterification of the product of hydrolysis of natural N'-lyso $GM_1$.

EXAMPLE 24

NATURAL N'-MYRISTOYL-N'-LYSO $GM_1$ 500 mg (0.33 mM) of natural N'-lyso $GM_1$ are dissolved in 50 ml of chloroform/methanol 1:1 and to this solution are added 0.5 ml of acetate buffer pH 5.7, 80 mM and 750 mg (1.7 mM) of myristic anhydride.

The condensation reaction is carried out at 25° C. for 18 hrs under constant stirring.

At the end of the reaction the product is dried, gathered with 5 ml of chloroform/methanol 1:1 and precipitated in 100 ml of acetone.

The raw product thus obtained is purified by preparative silica gel chromatography using as solvent a mixture of chloroform/methanol/water 60:20:3.

The pure fractions are pooled, evaporated, redissolved in 5 ml of chloroform/methanol 1:1, and the product is precipitated in 100 ml of acetone.

Natural N'-myristoyl-N'-lyso $GM_1$ is thus obtained: 500 mg (87.8% theoretical).

Chromatography on silica gel plates with a solvent of chloroform/methanol/calcium chloride 0.3% 60:35:8, shows the product to have Rf=0.53.

EXAMPLE 25

NATURAL N'-PALMITOYL-N'-LYSO $GM_1$ 500 mg (0.33 mM) of natural N'-lyso $GM_1$ are dissolved in 50 ml of chloroform/methanol 1:1 and to this solution are added 0.5 ml of acetate buffer pH 5.7, 80 mM and 900 mg (1.82 mM) of palmitic anhydride. The condensation reaction is carried out at 25° C. for 18 hrs under constant stirring.

At the end of the reaction the product is dried, gathered with 5 ml of chloroform/methanol 1:1 and precipitated in 100 ml of acetone.

The raw product thus obtained is purified by preparative silica gel chromatography using as solvent a mixture of chloroform/methanol/water 60:20:3.

The pure fractions are pooled, evaporated, and redissolved in 5 ml of chloroform/methanol 1:1 and the product is precipitated in 100 ml of acetone. Natural N'-palmitoyl-N'-lyso $GM_1$ is thus obtained: 520 mg (89.9% theoretical).

Chromatography on silica gel plates with a solvent of chloroform/methanol/$CaCl_2$ 0.3% 60:35:8, shows the product to have Rf=0.55.

EXAMPLE 26

NATURAL N'-STEAROYL-N'-LYSO $GM_1$ 500 mg (0.33 mM) of natural N'-lyso $GM_1$ are dissolved in 50 ml of chloroform/methanol 1:1 and to this solution are added 0.5 ml of acetate buffer pH 5.7, 80 mM and 100 mg (1.81 mM) of stearic anhydride dissolved in 20 ml of tetrahydrofuran.

The condensation reaction is conducted at 25° C. for 18 hrs under constant stirring.

At the end of the reaction the product is dried, gathered with 5 ml of chloroform/methanol 1:1 and precipitated in 100 ml of acetone.

The raw product thus obtained is purified by preparative silica gel chromatography using as solvent a mixture of chloroform/methanol/water 60:20:3.

The pure fractions are pooled, evaporated, and redissolved in 5 ml of chloroform/methanol 1:1, and the product is precipitated in 100 ml of acetone. Natural N'-stearoyl-N'-lyso $GM_1$ is thus obtained: 525 mg (83.4% theoretical).

Chromatography on silica gel plates with a solvent of chloroform/methanol/$CaCl_2$ 0.3% 60:35:8, shows the product to have Rf=0.57.

EXAMPLE 27

NATURAL N'-PIVALOYL-N'-LYSO $GM_1$ 500 mg (0.33 mM) of natural N'-lyso $GM_1$ are dissolved in 50 ml of chloroform/methanol 1:1 and to this solution are added 0.75 ml (0.54 mM) of triethylamine and 0.75 ml (6.75 mM) of pivalic anhydride.

The condensation reaction is conducted at 25° C. for 18 hrs under constant stirring.

At the end of the reaction the product is dried, gathered with 5 ml of chloroform/methanol 1:1 and precipitated in 100 ml of acetone. The raw product thus obtained is purified by preparative silica gel chromatography using as solvent a mixture of chloroform/methanol/water 60:20:3.

The pure fractions are pooled, evaporated, and redissolved in 5 ml of chloroform/methanol 1:1, and the product is precipitated in 100 ml of acetone.

Natural N'-pivaloyl-N'-lyso $GM_1$ is thus obtained: 440 mg (83.3% theoretical).

Chromatography on silica gel plates with a solvent of chloroform/methanol/$CaCl_2$ 0.3% 60:35:8, shows the product to have Rf=0.52.

EXAMPLE 28

NATURAL N'-PROPIONYL-N'-LYSO $GM_1$ 500 mg (0.33 mM) of natural N'-lyso $GM_1$ are dissolved in 50 ml of chloroform/methanol 1:1 and to this solution are added 0.5 ml of acetate buffer pH 5.7, 50 mM and 0.25 ml (1.95 mM) of propionic anhydride.

The condensation reaction is conducted at 25° C. for 18 hrs under constant stirring.

At the end of the reaction the product is dried, gathered with 5 ml of chloroform/methanol 1:1 and precipitated in 100 ml of acetone.

The raw product thus obtained is purified by silica gel preparative chromatography using as solvent a mixture of chloroform/methanol/water 60:20:3.

The pure fractions are pooled, evaporated, and redissolved in 5 ml of chloroform/methanol 1:1, and the product is precipitated in 100 ml of acetone. Natural N'-propionyl-N'-lyso $GM_1$ is thus obtained: 430 mg (82.8% theoretical).

Chromatography on silica gel plates with a solvent of chloroform/methanol/$CaCl_2$ 0.3% 60:35:8, shows the product to have Rf=0.45.

EXAMPLE 29

NATURAL N'-BUTYRYL'-LYSO $GM_1$ 500 mg (0.33 mM) of natural N'-lyso $GM_1$ are dissolved in 50 ml of chloroform/methanol 1:1 and to this solution are added 0.5 ml of acetate buffer pH 5.7, 50 mM and 0.25 ml (1.53 mM) of n-butyric anhydride.

The condensation reaction is conducted at 25° C. for 18 hrs under constant stirring.

At the end of the reaction the product is dried, gathered with 5 ml of chloroform/methanol 1:1 and precipitated in 100 ml of acetone.

The raw product thus obtained is purified by silica gel preparative chromatography using as solvent a mixture of chloroform/methanol/water 60:20:3.

The pure fractions are pooled, evaporated, and redissolved in 5 ml of chloroform/methanol 1:1, and the product is precipitated in 100 ml of acetone. Natural N'-butyryl-N'-lyso $GM_1$ is thus obtained: 450 mg (85.9% theoretical).

Chromatography on silica gel plates with a solvent of chloroform/methanol/$CaCl_2$ 0.3% 60:35:8, shows the product to have Rf=0.51.

EXAMPLE 30

NATURAL N'-ISOBUTYRYL-N'-LYSO $GM_1$ 500 mg (0.33 mM) of natural N'-lyso $GM_1$ are dissolved in 50 ml of chloroform/methanol 1:1 and to this solution are added 0.5 ml of acetate buffer pH 5.7, 50 mM and 0.25 ml (1.51 mM) of isobutyric anhydride.

The condensation reaction is conducted at 25° C. for 18 hrs under constant stirring.

At the end of the reaction the product is dried, gathered with 5 ml of chloroform/methanol 1:1 and precipitated in 100 ml of acetone.

The raw product thus obtained is purified by preparative silica gel chromatography using as solvent a mixture of chloroform/methanol/water 60:20:3.

The pure fractions are pooled, evaporated, and redissolved in 5 ml of chloroform/methanol 1:1, and the product is precipitated in 100 ml of acetone.

Natural N'-isobutyryl-N'-lyso $GM_1$ is thus obtained: 450 mg (85.9% theoretical). Chromatography on silica gel plates with a solvent of chloroform/methanol/calcium chloride 0.3% 60:35:8, shows the product to have Rf= 0.49.

EXAMPLE 31

NATURAL N'-LAUROYL-N'-LYSO $GM_1$ 500 mg (0.33 mM) of natural N'-lyso $GM_1$ are dissolved in 50 ml of chloroform/methanol 1:1 and to this solution are added 0.5 ml of acetate buffer pH 5.7, 50 mM and 600 mg (1057 mM) of lauric anhydride. The condensation reaction is conducted at 25° C. for 18 hrs under constant stirring.

At the end of the reaction the product is dried, gathered with 5 ml of chloroform/methanol 1:1 and precipitated in 100 ml of acetone.

The raw product thus obtained is purified by preparative silica gel chromatography using as solvent a mixture of chloroform/methanol/water 60:20:3.

The pure fractions are pooled, evaporated, and redissolved in 5 ml of chloroform/methanol 1:1, and the product is precipitated in 100 ml of acetone.

Natural N'-lauroyl-N'-lyso $GM_1$ is thus obtained: 495 mg (88.4% theoretical). Chromatography on silica gel plates with a solvent of chloroform/methanol/calcium chloride 0.3% 60:35:8, shows the product to have Rf= 0.51.

EXAMPLE 32

INNER ESTER OF N-PIVALOYL-N'-ACETYL-DI LYSO $GM_1$ 5 g (3.1 mM) of N-pivaloyl-N'-acetyl-di Lyso $GM_1$ are dissolved in 50 ml of N-methylpyrrolidone and to this solution are added 0.95 g (3.72 mM) of 2-chloro-1-methylpyridinium iodide and 0.52 ml (3.72 mM) of triethylamine under constant stirring.

Reaction is conducted for 18 hours at 4° C., after which the solution is filtered and precipitated in 500 ml of acetone.

The raw product thus obtained (4.7 g) is gathered with 25 ml of chloroform/isopropanol 1:1, filtered, precipitated in 125 ml of acetone and vacuum-dried.

Yield of inner ester of N-pivaloyl-N'-acetyl-di Lyso $GM_1$=4.5 g (91.2% theoretical).

After chromatography on silica gel plates with a solvent of chloroform/methanol/acetic acid 30:40:20, the product proves to be a unitary compound with Rf=0.42. Treatment with $Na_2CO_3$ 0.1N at 60° C. for 1 hr produces hydrolysis of the ester bond and the original ganglioside is reobtained.

The IR spectrum of the inner ester of N-pivaloyl N'-acetyl-di Lyso $GM_1$ performed using a KBr tablet, shows typical absorption at 1750 $cm^{-1}$ of the ester bond.

EXAMPLE 33

ETHYL ESTER OF N-PIVALOYL-N'-ACETYL-DI LYSO $GM_1$ 5 g (3.18 mM) of the inner ester of N-pivaloyl N'-acetyl-di Lyso $GM_1$ are dissolved in 200 ml of an anhydrous mixture of methylene/ethanol chloride 2:1. To this solution are added 184 mg (3.18 mM) of sodium ethylate dissolved in 50 ml of anhydrous ethanol and the mixture is left to reflux for 2 hrs.

At the end of the reaction the mixture is neutralized with anhydrous Dowex AG 50x8 resin, $H^+$ form, the resin is separated by filtration and washed with ethanol/methylene chloride 1:1 and the solution is then dried. The residue is gathered with 50 ml of methylene chloride/ethanol 1:1 and the product is precipitated with 250 ml of acetone.

The raw product thus obtained (4.9 g) is purified by preparative chromatography with Merck silica gel, using as solvent a mixture of chloroform/methanol/isopropanol/ammonium carbonate 2% 1140:620:180:140. The pure fractions are pooled, evaporated to dryness, and redissolved in 15 ml of chloroform/methanol 1:1, and the product is precipitated with 75 ml of acetone.

Yield of ethyl ester of N-pivaloyl-N'-acetyl di Lyso $GM_1$= 4.3 g (83.7% theoretical). Chromatography on silica gel plates with a solvent of chloroform/methanol/$CaCl_2$ 0.3% 60:35:8, shows the product to be a unitary compound with Rf 0.49. Treatment with $Na_2CO_3$ 0.1N at 60° C. for 1 hr produces hydrolysis of the ester bond and the original ganglioside is reobtained.

The IR spectrum of the ethyl ester of N-pivaloyl-N'-acetyl-di Lyso $GM_1$ performed with a KBr tablet, shows typical absorption at 1750 $cm^{-1}$.

EXAMPLE 34

ISOPROPYL ESTER OF N-PIVALOYL-N'-ACETYL-DI-LYSO $GM_1$ 5 g (3.18 mM) of the inner ester of N-pivaloyl N'-acetyl-di Lyso $GM_1$ are dissolved in 200 ml of an anhydrous mixture of methylene chloride/isopropanol 2:1. To this solution are added 261 mg (3.18 mM) of sodium isopropylate dissolved in 50 ml of anhydrous isopropanol and the mixture is left to reflux for 2 hrs.

After the reaction the mixture is neutralized with anhydrous Dowex resin AG 50x8 H$^+$ form, the resin is separated by filtration and washed with isopropanol/methylene chloride 1:1 and the solution is then dried. The residue is gathered with 50 ml of methylene chloride/isopropanol 1:1 and the product is precipitated with 250 ml of acetone.

The raw product thus obtained (4.9 g) is purified by medium pressure preparative chromatography (12 atm) with Merck silica gel, using as solvent a mixture of chloroform/methanol/isopropanol/ammonium carbonate 2% 1140:620:180:140. The pure fractions are pooled, evaporated to dryness, and redissolved in 15 ml of chloroform/methanol 1:1, and the product is precipitated with 75 ml of acetone.

Yield of isopropyl ester of N-pivaloyl-N'-acetyl-di Lyso $GM_1$=4.2 g (81.0% theoretical). Chromatography on silica gel plates with a solvent formed by chloroform/methanol/$CaCl_2$ 0.3% 60:35:8 shows the product to be a unitary compound with Rf 0.52. Treatment with $Na_2CO_3$ 0.1N at 60° C. for 1 hr causes hydrolysis of the ester bond and the original ganglioside is reobtained. The IR spectrum of the isopropyl ester of N-pivaloyl-N'-acetyl-di lyso $GM_1$ performed with a KBr tablet, shows typical absorption at 1750 $cm^{-1}$.

EXAMPLE 35

TERT-BUTYL ESTER OF N-PIVALOYL-N'-ACETYL-DI LYSO $GM_1$ 5 gr (3.18 mM) of the inner ester of N-pivaloyl-N'-acetyl-di Lyso $GM_1$ are dissolved in 200 ml of an anhydrous mixture of methylene chloride/tert-butanol. To this solution are added 305 mg (3.18 mM) of sodium tert-butylate dissolved in 50 ml of anhydrous tert-butanol and the mixture is left to reflux for 2 hrs.

After the reaction the mixture is neutralized with anhydrous Dowex resin AG 50x8 H$^+$ form, the resin is separated by filtration and washed with tert-butanol/methylene chloride 1:1 and the solution is then dried. The residue is gathered with 50 ml of methylene chloride/tert-butanol 1:1 and the product is precipitated with 250 ml of acetone.

The raw product thus obtained (4.9 g) is purified by medium pressure preparative chromatography (12 atm) with Merck silica gel, using as solvent a mixture of chloroform/methanol/isopropanol/ammonium carbonate 2% 1140:620:180:140. The pure fractions are pooled, evaporated to dryness, and redissolved in 15 ml of chloroform/methanol 1:1, and the product is precipitated with 75 ml of acetone.

Yield of tert-butyl ester of N-pivaloyl-N'-acetyl-di Lyso $GM_1$=4.1 g (78.4% theoretical).

After chromatography on silica gel plates with a solvent of chloroform/methanol/$CaCl_2$ 0.3% 60:35:8, the product proves to be a unitary compound with Rf 0.52. Treatment with $Na_2CO_3$ 0.1N at 60° C. for 1 hr causes hydrolysis of the ester bond and the original ganglioside is reobtained.

The IR spectrum of the terbutyl ester of N-pivaloyl-N'-acetyl-di Lyso $GM_1$ performed with a KBr tablet, shows typical absorption at 1750 $cm^{-1}$.

EXAMPLE 36

BENZYL ESTER OF N-PIVALOYL-N'-ACETYL-DI LYSO $GM_1$ 5 gr (3.14 mM) of the potassium salt of N-pivaloyl-N'-acetyl-di Lyso $GM_1$ are dissolved in 50 ml of dimethyl sulfoxide (DMSO) and to the solution are added 1.58 gr (12.5 mM) of benzyl chloride and 2.08 g (12.5 mM) of KJ. It is left to react in nitrogen for 24 hours at 25° C.

At the end of the reaction the solution is partitioned with n-butanol/water 2:1 to eliminate the DMSO and salts. The butanol solution is evaporated, the residue gathered with 50 ml of chloroform/benzyl alcohol 1:1 and the product of the reaction is precipitated with 250 ml of acetone.

The raw product thus obtained (5.3 g) is purified by preparative silica gel chromatography using as solvent a mixture of chloroform/methanol/water 65:32:7. The pure fractions are pooled, evaporated, and redissolved in 15 ml of chloroform/isopropanol 1:1, and the product is precipitated with 75 ml of acetone.

Yield of benzyl ester of N-pivaloyl-N'-acetyl di Lyso $GM_1$=4.8 g (91.0% theoretical). Chromatography on silica gel plates with a solvent of chloroform/methanol/$CaCl_2$ 0.3% 60:35:8, shows the product to be a unitary compound with Rf 0.65. Treatment with $Na_2CO_3$ 0.1N at 60° C. for 1 hr causes hydrolysis of the ester bond and the original ganglioside is reobtained.

The IR spectrum of the benzyl ester of N-pivaloyl-N'-acetyl-di Lyso $GM_1$ performed with a KBr tablet, shows typical absorption at 1750 cm–1 and UV spectroscopy using absolute ethyl alcohol shows three maximums at 250, 255 and 261 nm.

EXAMPLE 37

AMIDE OF N-PIVALOYL-N'-ACETYL-DI LYSO $GM_1$ 5 gr (3.18 mM) of the inner ester of N-pivaloyl-N'-acetyl-di Lyso $GM_1$ are suspended in 100 ml of anhydrous isopropyl alcohol. The suspension is stirred at a low temperature (−5° C.) and dry ammonia is bubbled through it under anhydrous conditions for 3 hrs. At the end of the reaction the solvent is eliminated by evaporation, the residue gathered with 50 ml of chloroform/methanol 1:1 and the reaction product is precipitated with 250 ml of acetone.

The raw product thus obtained (4.8 g) is treated with 100 ml of $Na_2CO_3$ 1% for 30 minutes at 25° C. to hydrolyze the residual ester groups, dialyzed in water, vacuum-dried and then purified by silica gel preparative chromatography using as first solvent a mixture of chloroform/methanol/water 60:40:9 and as second solvent a mixture of chloroform/methanol/water 55:45:10. The pure fractions, eluted and pooled, are evaporated, and dissolved in 15 ml of chloroform/methanol 1:1, and the amide precipitated with 75 ml of acetone.

Yield of amide of N-pivaloyl-N'-acetyl-di Lyso $GM_1$= 4.6 g (91.1% theoretical). After chromatography on silica gel plates with a solvent of chloroform/methanol/$CaCl_2$ 0.3% 60:35:8, the product proves to be a unitary compound with Rf 0.20.

The IR spectrum no longer presents the typical ester band at 1750 cm−1.

EXAMPLE 38

ETHYLAMIDE OF N-PIVALOYL-N'-ACETYL-DI LYSO $GM_1$ 5 gr (3.18 mM) of the inner ester of N-pivaloyl-N'-acetyl-di Lyso $GM_1$ are suspended in 100 ml of anhydrous isopropyl alcohol. The suspension is stirred at a low temperature (−5° C.) and dry ethylamine is bubbled through it under anhydrous conditions for 3 hrs. At the end of the reaction the solvent is eliminated by evaporation and the residue is gathered with 50 ml of chloroform/methanol 1:1 and the product of the reaction is precipitated with 250 ml of acetone.

The raw product thus obtained (4.9 g) is treated with 100 ml of $Na_2CO_3$ 1% for 30 minutes at 25° C. to hydrolyze the residue ester groups, dialyzed in water, vacuum-dried and then purified by preparative chromatography with Sephadex DEAE A25, acetate form, using as solvent a mixture of chloroform/methanol/water 30:60:8. The pooled neutral fractions are evaporated, dissolved in 15 ml of chloroform/methanol 1:1 and the amide precipitated with 75 ml of acetone.

Yield of ethylamide of N-pivaloyl-N'-acetyl-di Lyso $GM_1$=4.7 g (91.5% theoretical). Chromatography on silica gel plates with a solvent of chloroform/methanol/$CaCl_2$ 0.3% 60:35:8, shows the product to be a unitary compound with Rf 0.46. The IR spectrum no longer presents the typical ester band at 1750 $cm^{-1}$.

EXAMPLE 39

ISOPROPYLAMIDE OF N-PIVALOYL-N'-ACETYL-DI-LYSO $GM_1$ 5 gr (3.18 mM) of the inner ester of N-pivaloyl-N'-acetyl-di Lyso $GM_1$ are dissolved in 25 ml of anhydrous isopropylamine and the mixture is stirred under anhydrous conditions for 24 hours at 25° C.

At the end of the reaction the solvent is eliminated by evaporation and the residue is gathered with 50 ml of chloroform/methanol 1:1 and the reaction product is precipitated with 250 ml of acetone.

The raw product thus obtained (4.8 g) is treated with 100 ml of $Na_2CO_3$ 1% for 30 minutes at 25° C. to hydrolyze the residual ester groups, dialyzed in water, vacuum-dried and then purified by preparative chromatography on a silica gel column using as solvent a mixture of chloroform/methanol/ammonia 25N 60:40:9. The pure fractions, eluted and pooled, are evaporated, dissolved in 15 ml of chloroform/methanol 1:1 and the product precipitated with 75 ml of acetone.

Yield of isopropylamide of N-pivaloyl-N'-acetyl-di Lyso $GM_1$=4.2 g (81.1% theoretical).

Chromatography on silica gel plates with a solvent formed by chloroform/methanol/$CaCl_2$ 0.3% 60:35:8, shows the product to be a unitary compound with Rf 0.66. The IR spectrum no longer presents the typical ester band at 1750 $cm^{-1}$.

EXAMPLE 40

2-BUTYLAMIDE OF N-PIVALOYL-N'-ACETYL-DI LYSO $GM_1$ 5 gr (3.18 mM) of the inner ester of N-pivaloyl N'-acetyl-di Lyso $GM_1$ are dissolved in 25 ml of anhydrous pyridine and to the solution are added 12.5 ml of 2-butylamine and the mixture is stirred under anhydrous conditions for 24 hours at 25° C.

At the end of the reaction the solvent is eliminated by evaporation and the residue is gathered with 50 ml of chloroform/methanol 1:1 and the product of the reaction precipitated with 250 ml of acetone.

The raw product thus obtained (5.2 g) is treated with 100 ml of $Na_2CO_3$ 1% for 30 minutes at 25° C. to hydrolyze the residual ester groups, dialyzed in water, vacuum-dried and then purified by preparative silica gel chromatography using as solvent a mixture of chloroform/methanol/water 110:40:6. The pure fractions are eluted, pooled, evaporated, dissolved in 15 ml of chloroform/methanol 1:1 and the amide precipitated with 75 ml of acetone.

Yield of 2-butylamide of N-pivaloyl-N'-acetyl-di Lyso $GM_1$=4.7 g (88.1% theoretical).

Chromatography on silica gel plates with a solvent of chloroform/methanol/$CaCl_2$ 0.3% 60:35:8, shows the product to be a unitary compound with Rf 0.50. The IR spectrum no longer presents the typical ester band at 1750 $cm^{-1}$.

EXAMPLE 41

DIMETHYLAMINOETHYLAMIDE OF N-PIVALOYL-N'-ACETYL-DI LYSO $GM_1$ 5 gr (3.18 mM) of the inner ester of N-pivaloyl N'-acetyl-di Lyso $GM_1$ are dissolved in 50 ml of an anhydrous solution of chloroform/isopropanol 1:1 after which are added 599 mg (6.36 mM) of dimethylaminoethylamine. The solution is stirred under anhydrous conditions for 24 hours at 25° C. At the end of the reaction the solvent is eliminated by evaporation and the residue is gathered with 50 ml of chloroform/methanol 1:1 and the product of the reaction is precipitated with 250 ml of acetone.

The raw product thus obtained (5.2 g) is treated with 100 ml of $Na_2CO_3$ 1% for 30 minutes at 25° C. to hydrolyze the residual ester groups, dialyzed in water, vacuum-dried and then purified using as first solvent a mixture of chloroform/methanol/ammonia 2.5N 60:40:9 and as second solvent chloroform/methanol/water 60:40:9. The pure, eluted fractions are pooled, evaporated, dissolved in 15 ml of chloroform/methanol 1:1 and the amide precipitated with 75 ml of acetone.

Yield of dimethylaminoethylamide of N-pivaloyl-N'-acetyl-di Lyso $GM_1$=4.9 g (92.9% theoretical).

Chromatography on silica gel plates with a solvent of chloroform/methanol/$CaCl_2$ 0.3% 60:35:8, shows the product to be a unitary compound with Rf 0.14.

The IR spectrum no longer presents the typical ester band at 1750 $cm^{-1}$.

EXAMPLE 42

DIETHYLAMIDE OF N-PIVALOYL-N'-ACETYL-DI LYSO $GM_1$ 5 gr (3.18 mM) of the inner ester of N-pivaloyl-N'-acetyl-di Lyso $GM_1$ are dissolved in 25 ml of diethylamine. The mixture is stirred under anhydrous conditions at a low temperature (–5° C.) for 24 hrs. At the end of the reaction the solvent is eliminated by evaporation and the residue is gathered with 50 ml of chloroform/methanol 1:1 and the product of the reaction is precipitated with 250 ml of acetone.

The raw product thus obtained (5.1 g) is treated with 100 ml of $Na_2CO_3$ 1% for 30 minutes at 25° C. to hydrolyze the residual ester groups, dialyzed in water, vacuum-dried and then purified using as first solvent a mixture of chloroform/methanol/ammonia 2.5N 60:40:9 and as second solvent chloroform/methanol/water 60:40:9. The pure, eluted fractions are pooled, evaporated, dissolved in 15 ml of chloroform/methanol 1:1 and the amide precipitated with 75 ml of acetone.

Yield of diethylamide of N-pivaloyl-N'-acetyl-di Lyso $GM_1$=4.7 gr (90.0% theoretical).

Chromatography on silica gel plates with a solvent of chloroform/methanol/$CaCl_2$ 0.3% 60:35:8, shows the product to be a unitary compound with Rf 0.50. The IR spectrum no longer presents the typical ester band at 1750 $cm^{-1}$.

EXAMPLE 43

ETHANOLAMIDE OF N-PIVALOYL-N'-ACETYL-DI LYSO $GM_1$ 5 gr (3.18 mM) of the inner ester of N-pivaloyl-N'-acetyl-di Lyso $GM_1$ are dissolved in 50 ml of an anhydrous solution of chloroform/isopropanol 1:1 and to this solution are added 388 mg (6.36 mM) of ethanolamine and the mixture is kept under anhydrous conditions and constantly stirred at 25° C.

At the end of the reaction the solvent is eliminated by evaporation and the residue is gathered with 50 ml of chloroform/methanol 1:1 and the product of the reaction is precipitated with 250 ml of acetone.

The raw product thus obtained (5.1 g) is treated with 100 ml of $Na_2CO_3$ 1% for 30 minutes at 25° C. to hydrolyze the residual ester groups, dialyzed in water, vacuum-dried and then purified using as first solvent a mixture of chloroform/methanol/ammonia 2.5N 60:40:9 and as second solvent chloroform/methanol/water 60:40:9. The pure, eluted fractions are pooled, evaporated, dissolved in 15 ml of chloroform/methanol 1:1 and the amide precipitated with 75 ml of acetone.

Yield of ethanolamide of N-pivaloyl-N'-acetyl-di Lyso $GM_1$=4.8 g (82.5% theoretical).

Chromatography on silica gel plates with a solvent of chloroform/methanol/$CaCl_2$ 0.3% 60:35:8, shows the product to be a unitary compound with Rf 0.49. The IR spectrum no longer presents the typical ester band at 1750 $cm^{-1}$.

EXAMPLE 44

BENZYLAMIDE OF N-PIVALOYL-N'-ACETYL-DI LYSO $GM_1$ 5 gr (3.18 mM) of the inner ester of N-pivaloyl-N'-acetyl-di Lyso $GM_1$ are dissolved in 20 ml of anhydrous pyridine and to the solution are added 374 mg (3.50 mM) of benzylamine and the solution is stirred under anhydrous conditions for 24 hours at 25° C. At the end of the reaction the solvent is eliminated by evaporation, the residue is gathered with 50 ml of chloroform/methanol 1:1 and the product of the reaction is precipitated with 250 ml of acetone.

The raw product thus obtained (5.1 g) is treated with 100 ml of $Na_2CO_3$ 1% for 30 minutes at 25° C. to hydrolyze the residual ester groups, dialyzed in water, vacuum-dried and then purified by preparative chromatography with Sephadex DEAE A25, acetate form, using as solvent a mixture of chloroform/methanol/water 30.60.8. The pooled neutral fractions are evaporated, dissolved in 15 ml of chloroform/methanol 1:1 and the amide precipitated with 75 ml of acetone.

Yield of benzylamide of N-pivaloyl-N'-acetyl-di Lyso $GM_1$=4.6 g (78.8% theoretical).

Chromatography on silica gel plates with a solvent of chloroform/methanol/$CaCl_2$ 0.3% 60:35:8, shows the product to be a unitary compound with Rf 0.69. The IR spectrum no longer presents the typical ester band at 1750 $cm^{-1}$.

EXAMPLE 45

PERACETYLATE OF THE ETHYL ESTER OF N-PIVALOYL-N'-ACETYL-DI LYSO $GM_1$ 5 gr (3.09 μM) of the ethyl ester of N-pivaloyl-N'-acetyl-di Lyso $GM_1$ are dissolved in 50 ml of anhydrous pyridine and to the solution are added, at 25° C., 25 ml of freshly distilled acetic anhydride. The solution is kept under constant stirring for 72 hrs at room temperature. At the end of the reaction the solution is vacuum-dried and the residue is partitioned between 100 ml of iced water and 200 ml of ethyl acetate. The ethyl acetate is then washed with cold HCl 0.1M, with water and with a solution of $NaHCO_3$ 0.1M. The organic phases are then anhydrified with sodium sulphate, vacuum-dried and the residue is purified by preparative chromatography on a silica gel column using a mixture of dichloromethane/ethyl acetate/isopropanol 70:30:45 as elution solvent. The pure fractions are pooled, evaporated, and redissolved in 20 ml of ethyl ether and precipitated in 100 ml of di- normal hexane.

Yield of the peracetylate of the ethyl ester of N-pivaloyl-N'-acetyl-di Lyso $GM_1$=4.5 g (63.2% theoretical).

Chromatography on silica gel plates with a solvent formed by chloroform/ethyl acetate/methanol 70:30:10 and ethyl acetate/isopropanol 95:5 shows the product to be a unitary compound with Rf 0.49 and 0.28 respectively.

EXAMPLE 46

PREPARATION OF A GANGLIOSIDE MIXTURE (GA) BY EXTRACTION OF BOVINE BRAIN TISSUE

Bovine brain tissue, extracted from the animal, is homogenized in phosphate buffer at pH 6.8. 6 volumes of tetrahydrofuran are then added and the resulting mixture is centrifuged. The upper layer is extracted twice with tetrahydrofuran. After centrifugation the non-polar materials are removed by partitioning with ethyl ether and the aqueous tetrahydrofuran phase is introduced into an ion exchange column equilibrated with 50% ethanol. Barium hydroxide and four volumes of ice-cold ethanol are added to the effluent from the column. After refrigeration for 18 hours a precipitate is gathered which is then lightly acidified with hydrochloric acid dissolved in water. The solution thus obtained is dialyzed and freeze-dried. The yield at this point is approximately 0.6 mg of raw ganglioside mixture per gram of nervous tissue used. The freeze-dried powder is dispersed in 20 volumes of chloroform-methanol 2:1, the solution obtained is filtered until completely clear, and then partitioned adding 0.2 volumes of a solution of potassium chloride in water at 0.88%.

The upper layer is separated, dialyzed and freeze-dried. The final yield is approximately 0.3 mg of a purified mixture of ganglioside salts per gram of brain tissue.

The ganglioside mixture obtained can be fractioned into various portions representing substantially pure gangliosides (in the sense used in the general description), using silicic acid columns and eluting with mixtures of methanol-chloroform. On average, the following composition was thus obtained: 40% of ganglioside GD1a, 21% of ganglioside $GM_1$, 19% of ganglioside GT1b and 16% of ganglioside GD1b.

EXAMPLE 47

N,N'-DI-ACETYL DERIVATIVES OF A MIXTURE OF N,N'-DI LYSO GANGLIOSIDES 10 gr (5.3 mM) of ganglioside mixture (obtained according to Example 46) are dissolved in 200 ml of a solution of 0.75M of KOH in n-propyl alcohol. Hydrolysis is conducted at 93° C. for 24 hrs. At the end of the reaction it is neutralized with acetic acid, precipitated in 2 liters of acetone and dried. The product thus obtained is then dialyzed to a constant volume (100 ml), partitioned with 5 volumes of chloroform/methanol 2:1 and precipitated again in acetone.

The intermediate reaction product thus obtained is redissolved in 500 ml of chloroform/methanol/water 1:1:0.1. To this solution are added 2.08 ml (15 mM) of triethylamine and 1.4 ml (15 mM) of acetic anhydride. It is left to react for 2 hrs at room temperature.At the end of reaction it is dried, gathered with 10 ml of chloroform/methanol 1:1 and precipitated in 100 ml of acetone.

Product obtained=8.9 gr (95% theoretical).

EXAMPLE 48

PHARMACEUTICAL PREPARATIONS IN INJECTABLE SOLUTIONS

Preparation No. 1—one 2 ml vial contains:

| active substance | mg 5 |
| sodium chloride | mg 16 |
| citrate buffer pH 6 in | ml 2 |
| distilled water to make | |

The active substance is chosen from the group formed by the ganglioside derivatives described in any one of Examples 4, 13 and 14.
Preparation No. 2—one 2 ml vial contains:

| active substance | mg 50 |
| sodium chloride | mg 16 |
| citrate buffer pH 6 in | ml 2 |
| distilled water to make | |

The active substance is chosen from the group formed by the ganglioside derivatives described in any one of Examples 9, 16, 23, 28, 29 and 30.
Preparation No. 3—one 4 ml flacon contains:

| active substance | mg 100 |
| sodium chloride | mg 32 |
| citrate buffer pH 6 in | ml 4 |
| distilled water to make | |

The active substance is chosen from the group formed by the ganglioside derivatives described in any one of Examples 5, 6, 15 and 27.
Preparation Nos. 1, 2 and 3 can be administered directly to animals or humans by any one of the described routes. Furthermore, the compounds can contain other pharmaceutically active substances.

EXAMPLE 49

PHARMACEUTICAL COMPOSITIONS IN TWIN FLACONS

The preparations illustrated in this Example are presented in twin flacons. The first flacon contains the active substance in the form of a freeze-dried powder in quantities varying between 10% and 90% in weight together with a pharmaceutically acceptable excipient, with glycine or mannitol. The second flacon contains the solvent, as a solution of sodium chloride and a citrate buffer.

Immediately before administration the contents of the two flacons are mixed and the freeze-dried powder of the active substance is rapidly dissolved, giving an injectable solution. The pharmaceutical form where the freeze-dried powder of the active substance is contained in a flacon, is the preferred form of the present invention.
System No.1
a. one 2 ml flacon of freeze-dried powder contains:

| active substance | mg 5 |
| glycine | mg 30 | b. one 2 ml vial of solvent contains:

| sodium chloride | mg 16 |
| citrate buffer in distilled water to make | ml 2 |

The active substance is chosen from the group formed by the ganglioside derivatives described in any one of Examples 32 and 33.
System No.2
a. one 3 ml vial of freeze-dried powder contains:

| | |
|---|---|
| active substance | mg 5 |
| mannitol | mg 40 | b. one 2 ml vial of solvent contains:

| | |
|---|---|
| sodium chloride | mg 16 |
| citrate buffer in distilled water to make | ml 2 |

The active substance is chosen from the group formed by the ganglioside derivatives described in any one of Examples 32 and 33.
System No. 3
a. one 3 ml vial of freeze-dried powder contains:

| | |
|---|---|
| active substance | mg 50 |
| glycine | mg 25 | b. one 3 ml vial of solvent contains:

| | |
|---|---|
| sodium chloride | mg 24 |
| citrate buffer in distilled water to make | ml 3 |

The active substance is chosen from the group formed by the ganglioside derivatives described in Examples 34 and 36.
System No. 4
a. one 3 ml vial of freeze-dried powder contains:

| | |
|---|---|
| active substance | mg 50 |
| mannitol | mg 20 | b. one 3 ml vial of solvent contains:

| | |
|---|---|
| sodium chloride | mg 24 |
| citrate buffer in distilled water to make | ml 3 |

The active substance is chosen from the group formed by the ganglioside derivatives described in Examples 34 and 36.
System No. 5
a. one 5 ml flacon of freeze-dried powder contains:

| | |
|---|---|
| active substance | mg 150 |
| glycine | mg 50 | b. one 4 ml vial of solvent contains:

| | |
|---|---|
| sodium chloride | mg 32 |
| citrate buffer in distilled water to make | ml 4 |

The active substance is chosen from the group formed by the ganglioside derivatives described in any one of Examples 44 and 45.
System No. 6
a. one 5 ml flacon of freeze-dried powder contains:

| | |
|---|---|
| active substance | mg 100 |
| mannitol | mg 40 | b. one 4 ml vial of solvent contains:

| | |
|---|---|
| sodium chloride | mg 32 |
| citrate buffer in distilled water to make | ml 4 |

The active substance is chosen from the group formed by the ganglioside derivatives described in any one of Examples 44 and 45.
System No. 7
a. one 3 ml flacon contains:

| | |
|---|---|
| sterile, micronized active substance | mg 40 | b. one 3 ml vial of solvent contains:

| | |
|---|---|
| Tween 80 | mg 10 |
| sodium chloride | mg 24 |
| phosphate buffer in distilled water to | ml 3 |

The active substance is chosen from the group formed by the ganglioside derivatives described in Examples 37 and 38.
System No. 8
a. one 5 ml flacon contains:

| | |
|---|---|
| sterile, micronized active substance | mg 100 | b. one 4 ml vial of solvent contains:

| | |
|---|---|
| Tween 80 | mg 5 |
| soybean lecithin | mg 5 |
| sodium chloride | mg 36 |
| citrate buffer in distilled water to make | ml 4 |

The active substance is chosen from the group formed by the ganglioside derivatives described in any one of Examples 40 and 42.

EXAMPLE 50

PHARMACEUTICAL PREPARATIONS FOR TRANSDERMAL ADMINISTRATION

Preparation No.1—one plaster contains:

| | |
|---|---|
| active substance | mg 100 |
| glycerin | g 1.6 |
| polyvinyl alcohol | mg 200 |
| polyvinylpyrrolidone | mg 100 |
| excipient to aid transdermal penetration | mg 20 |
| water | g 1.5 |

The active substance is chosen from the group formed by the ganglioside derivatives described in any one of Examples 32, 33 and 34.

Preparation No. 2—100 gr of ointment contain:

| | |
|---|---|
| active substance (in 5 gr of mixed phospholipid liposomes) | g 4.0 |
| polyethylene glycol monostearate | g 1.5 |
| glycerin | g 1.5 |
| p-hydroxybenzoic acid ester | mg 125 |
| water | g 72.9 |

The active substance is chosen from the group formed by the ganglioside derivatives described in any one of Examples 32, 33 and 34.

EXAMPLE 51

PHARMACEUTICAL PREPARATIONS FOR ORAL ADMINISTRATION

Preparation No. 1—one tablet contains:

| | |
|---|---|
| active substance | mg 20 |
| microcrystalline cellulose | mg 150 |
| lactose | mg 20 |
| amide | mg 10 |
| magnesium stearate | mg 5 |

The active substance is chosen from the group formed by the ganglioside derivatives described in any one of Examples 1, 2, 3, 8 and 11.

Preparation No. 2—one tablet contains:

| | |
|---|---|
| active substance | mg 30 |
| carboxymethyl cellulose | mg 150 |
| amide | mg 15 |
| shellac | mg 10 |
| sucrose | mg 35 |
| coloring | mg 0.5 |

The active substance is chosen from the group formed by the ganglioside derivatives described in any one of Examples 13 and 23.

Preparation No. 3—one gelatinous capsule contains:

| | |
|---|---|
| active substance | mg 40 |
| lactose | mg 100 |
| gastroresistant coating | mg 5 |

The active substance is chosen from the group formed by the ganglioside derivatives described in any one of Examples 35, 41 and 47.

Preparation No. 4—one soft gelatin capsule contains:

| | |
|---|---|
| active substance | mg 50 |
| vegetable oil | mg 200 |
| beeswax | mg 20 |
| gelatin | mg 150 |
| glycerin | mg 50 |
| coloring | mg 3 |

The active substance is chosen from the group formed by the ganglioside derivatives described in any one of Examples 35, 41 and 47.

The following is claimed:

1. A pharmaceutical composition comprising, as active ingredient, N,N'-diacetyl-N,N'-di-lyso $GM_1$, together with a pharmaceutically acceptable excipient, wherein said pharmaceutical composition is in solid or semisolid form.

2. The pharmaceutical composition according to claim 1, wherein said solid or semisolid form is selected from the group consisting of a pill, a tablet, a jelly-like capsule, a suppository, a soft gelatin capsule, a cream, an ointment, and a plaster.

3. A method of inhibiting glutamate-induced neurotoxicity, which comprises administering an effective amount of a pharmaceutical composition comprising N,N'-diacetyl-N,N' -di-lyso $GM_1$, together with a pharmaceutically acceptable excipient, to a patient in need thereof.

4. The method according to claim 3, in which said glutamate-induced neurotoxicity is caused by cortical damage.

5. The method according to claim 3, in which said glutamate-induced neurotoxicity is caused by ischemia.

6. The method according to any one of claims 3, 4, or 5, in which from 0.05 to 5 mg of said N,N'-diacetyl-N,N'-di-lyso $GM_1$ per kg of body weight of the patient are administered daily by the parenteral route.

* * * * *